US011740243B2

(12) United States Patent
In-San et al.

(10) Patent No.: US 11,740,243 B2
(45) Date of Patent: Aug. 29, 2023

(54) EARLY AND NON INVASIVE METHOD FOR ASSESSING A SUBJECT'S RISK OF HAVING PANCREATIC DUCTAL ADENOCARCINOMA AND METHODS OF TREATMENT OF SUCH DISEASE

(71) Applicants: INSERM (Institut National de la Sante et de la Recherche Medicale), Paris (FR); Centre National de la Recherche Scientifique (CNRS), Paris (FR); Universite Claude Bernard—Lyon 1, Villeurbanne (FR); Centre Leon Berard, Lyons (FR); KIST (Korea Institute of Science and Technology), Seoul (KR)

(72) Inventors: Kim In-San, Seoul (KR); Philippe Bertolino, Lyons (FR); Ana Hennino, Lyons (FR)

(73) Assignees: INSERM (INSTITUT NATIONAL DE LA SANTÉ ET DE LA RECHERCHE MÉDICALE), Paris (FR); CENTRE NATIONAL DE LA RECHERCHE SCIENTIFIQUE (CNRS), Paris (FR); UNIVERSITÉ CLAUDE BERNARD—LYON, Villeurbanne (FR); CENTRE LEON BERARD, Lyons (FR); KIST (KOREA INSTITUTE OF SCIENCE AND TECHNOLOGY), Seoul (KR)

( * ) Notice: Subject to any disclaimer, the term of this patent is extended or adjusted under 35 U.S.C. 154(b) by 713 days.

(21) Appl. No.: 16/081,462

(22) PCT Filed: Mar. 15, 2017

(86) PCT No.: PCT/EP2017/056150
§ 371 (c)(1),
(2) Date: Aug. 31, 2018

(87) PCT Pub. No.: WO2017/158043
PCT Pub. Date: Sep. 21, 2017

(65) Prior Publication Data
US 2019/0086417 A1 Mar. 21, 2019

(30) Foreign Application Priority Data
Mar. 15, 2016 (EP) .................................... 16305276

(51) Int. Cl.
*G01N 31/00* (2006.01)
*G01N 33/53* (2006.01)
*G01N 33/574* (2006.01)

(52) U.S. Cl.
CPC .............. *G01N 33/57438* (2013.01)

(58) Field of Classification Search
None
See application file for complete search history.

(56) References Cited

U.S. PATENT DOCUMENTS

2013/0309255 A1  11/2013  Castronovo

FOREIGN PATENT DOCUMENTS

| JP | 2013545992 A | 11/2013 | |
| WO | 2006/092729 A2 | 9/2006 | |
| WO | WO-2006092729 A2 * | 9/2006 | ....... G01N 33/57438 |
| WO | 2012/079977 A1 | 6/2012 | |
| WO | 2012079977 A1 | 6/2012 | |
| WO | WO-2012079977 A1 * | 6/2012 | ....... G01N 33/57438 |
| WO | 2014/113406 A1 | 7/2014 | |
| WO | WO-2014113406 A1 * | 7/2014 | ........... A61K 31/713 |
| WO | 2015200790 A1 | 12/2015 | |

OTHER PUBLICATIONS

Bae et al. (Acta Physiol 2014, 212, 306-315) (Year: 2014).*
Bae etal (Acta Physiol 2014 32127. 306-315) (Year: 2014).*
Neuzillet et al. (Oncotarget, Jan. 2014, vol. 5, No. 1, pp. 78-94) (Year: 2014).*
Turtoi et al. (Journal of Proteome Research, 2011, vol. 10, pp. 4302-4313) (Year: 2011).*
Turtoi et al.; "Identification of Novel Accessible Proteins Bearing Diagnostic and Therapeutic Potential in Human Pancreatic Ductal Adenocarcinoma"; Journal of Proteome Research, vol. 10, No. 9, Sep. 2, 2011, pp. 4302-4313.

(Continued)

*Primary Examiner* — Lisa V Cook
(74) *Attorney, Agent, or Firm* — WC&F IP

(57) ABSTRACT

A non invasive diagnostic method of pancreatic ductal adenocarcinoma (PDAC) in a subject is provided. The method comprises the step of measuring the level of βig-h3 protein in a blood sample wherein the serum level of βig-h3 is positively correlated with the risk of having a PDAC. By following studies on 2 distinct cohorts of 20 and 104 of PDAC patients, and on PDAC mouse model, the inventors show that βig-h3 can be directly detected in the blood sample and βig-h3 is expressed very early in tumorigenesis in pancreatic neoplastic lesions. Also provided is a βig-h3 protein, for use in the treatment of PDAC. The inventors found that βig-h3 bind directly on CD8$^+$ T cells by reducing their activation and cytotoxic properties. Furthermore, the use of neutralizing βig-h3 antibodies in PDAC mouse model reduced tumor growth by enhancing CD8$^+$ T cell anti-tumoral response. Thus, neutralizing βig-h3 which acts as a novel immunological check-point target in PDAC therefore allows to restore beneficial anti-tumor immunity in PDAC.

Figure 2A:
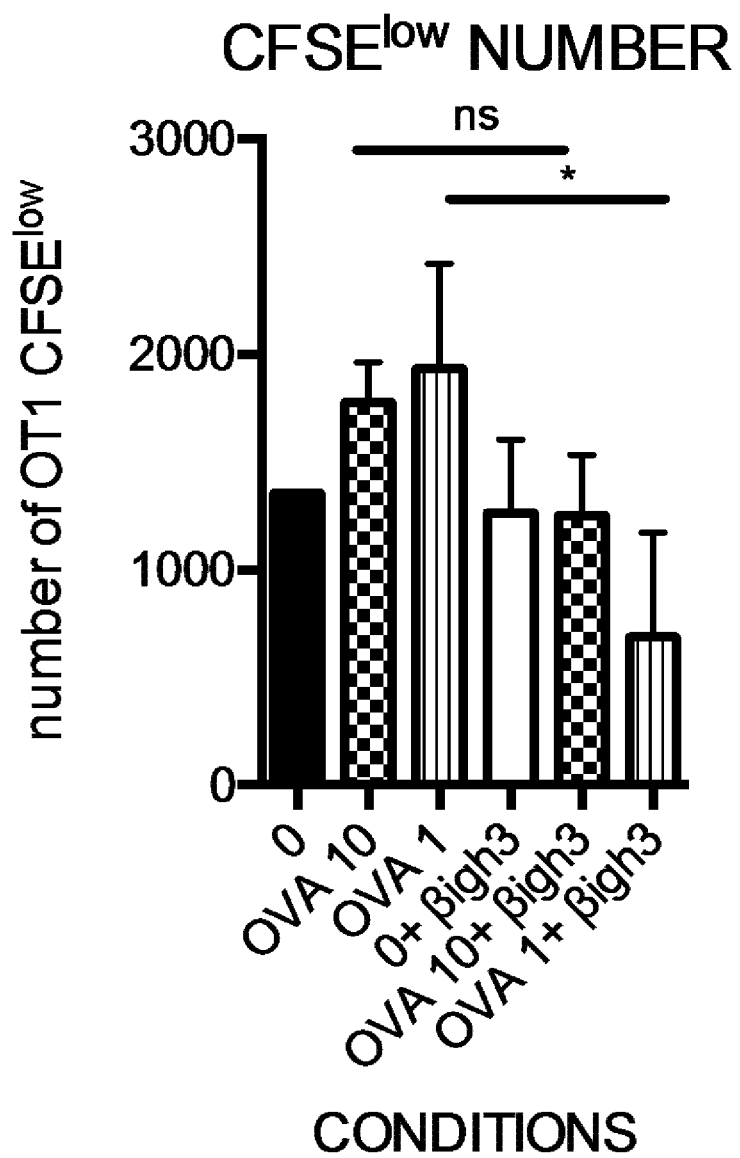
Figure 2B:
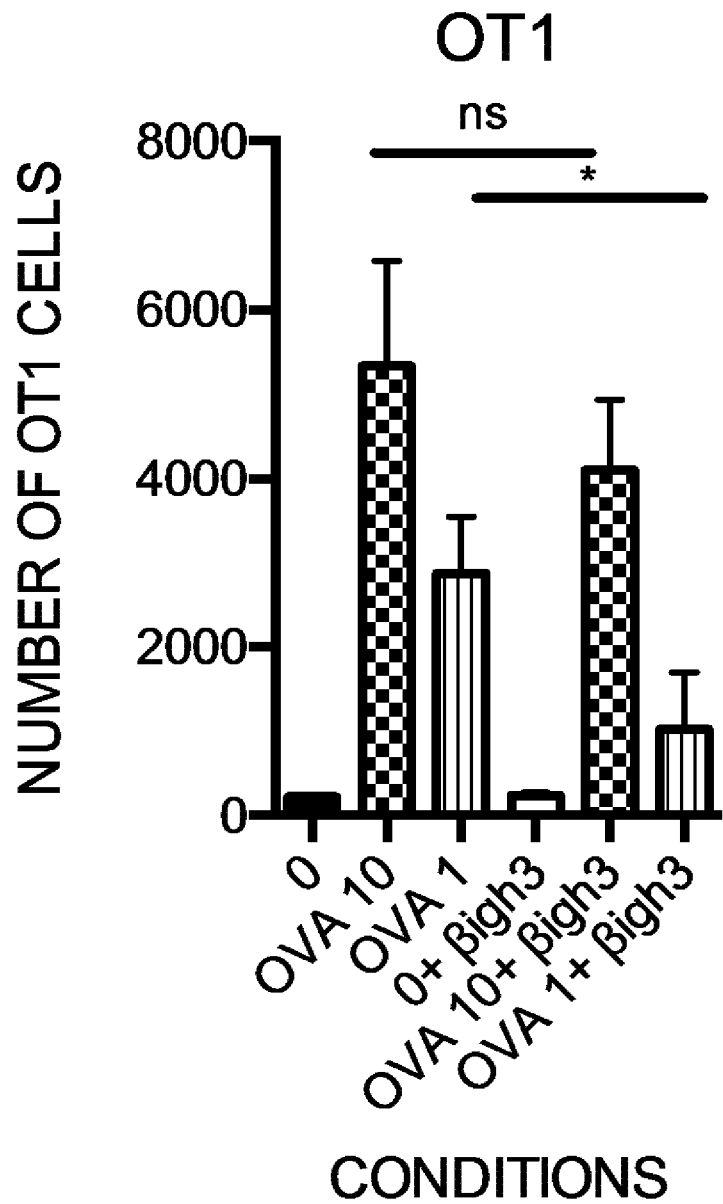

12 Claims, 19 Drawing Sheets
Specification includes a Sequence Listing.

(56) References Cited

OTHER PUBLICATIONS

Chang et al.; "Secretome-Based Identification of ULBP2 as a Novel Serum Marker for Pancreatic Cancer Detection"; PLoS One, vol. 6, No. 5, May 20, 2011, p. e29929.

* cited by examiner

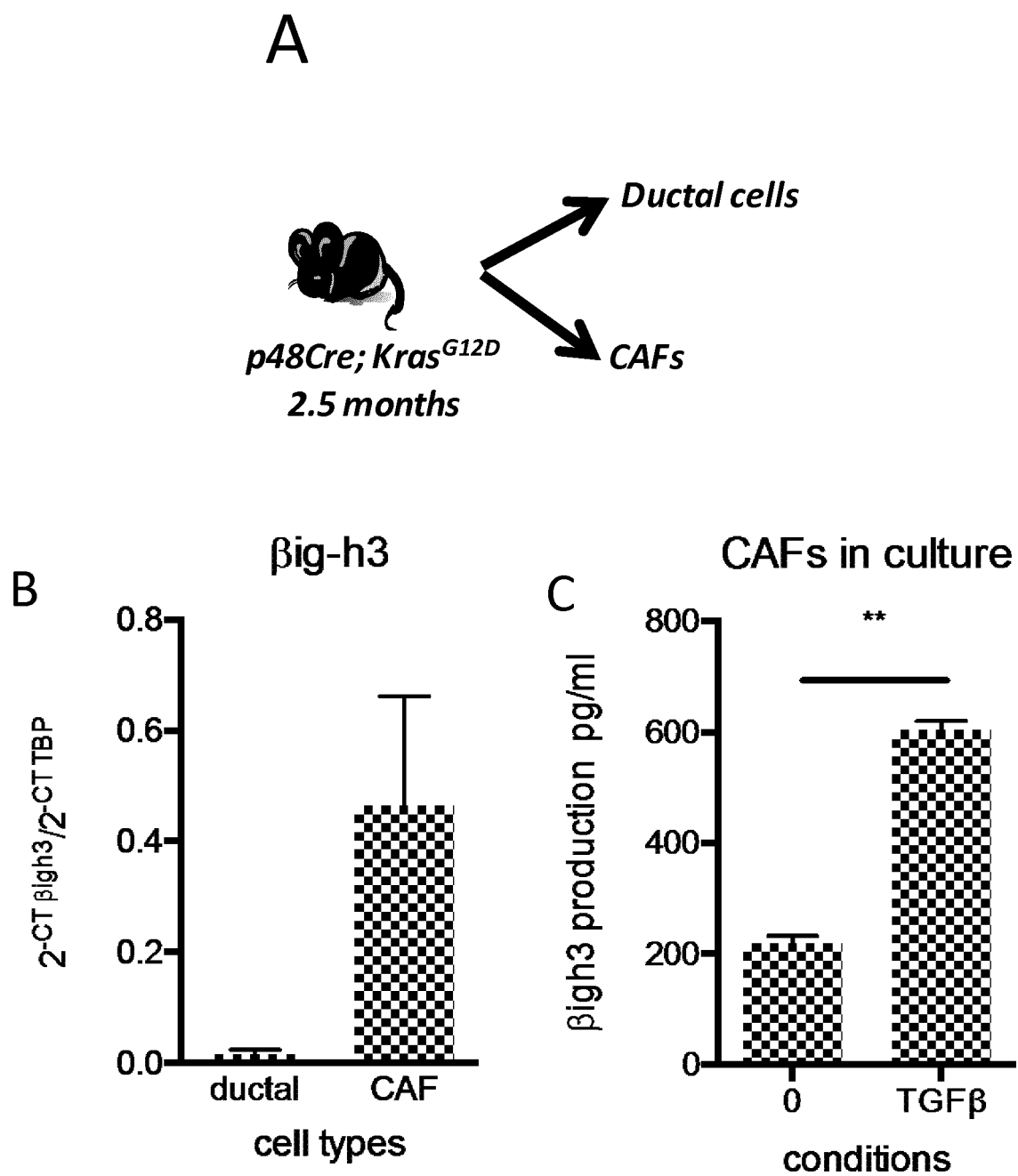
Figure 1 A, B and C

A

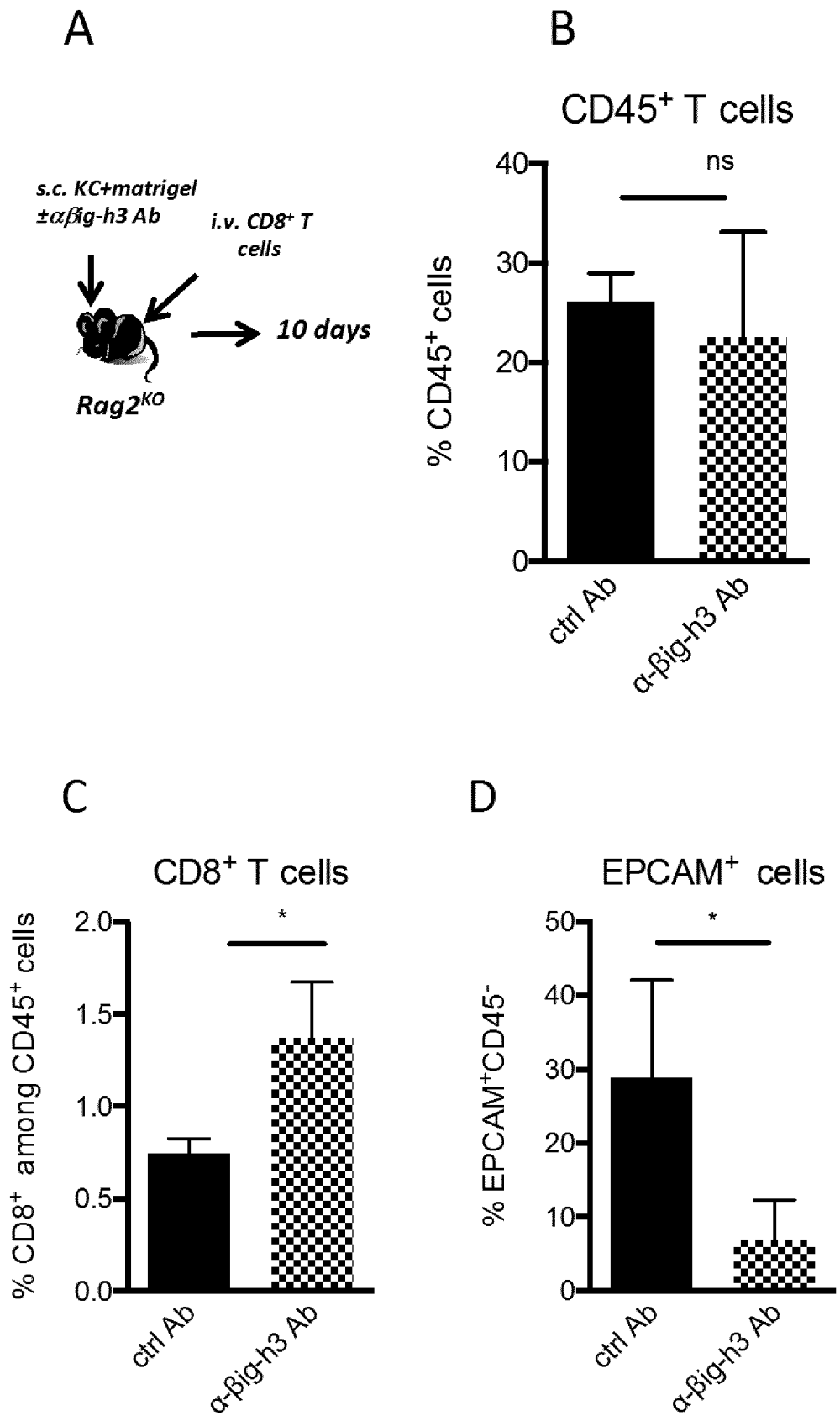
Figure 6A-D

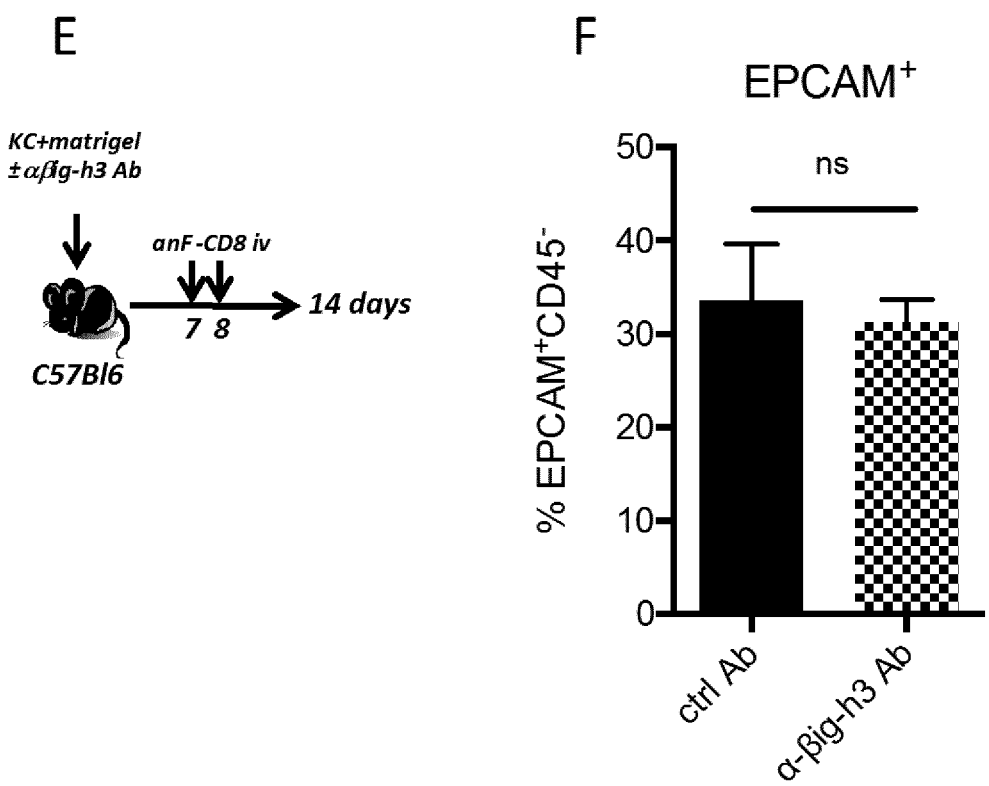
Figure 6E-F

A
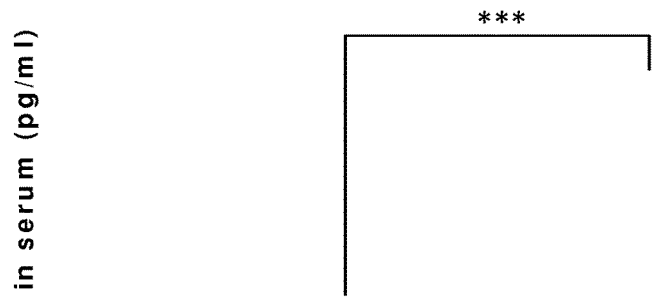
B
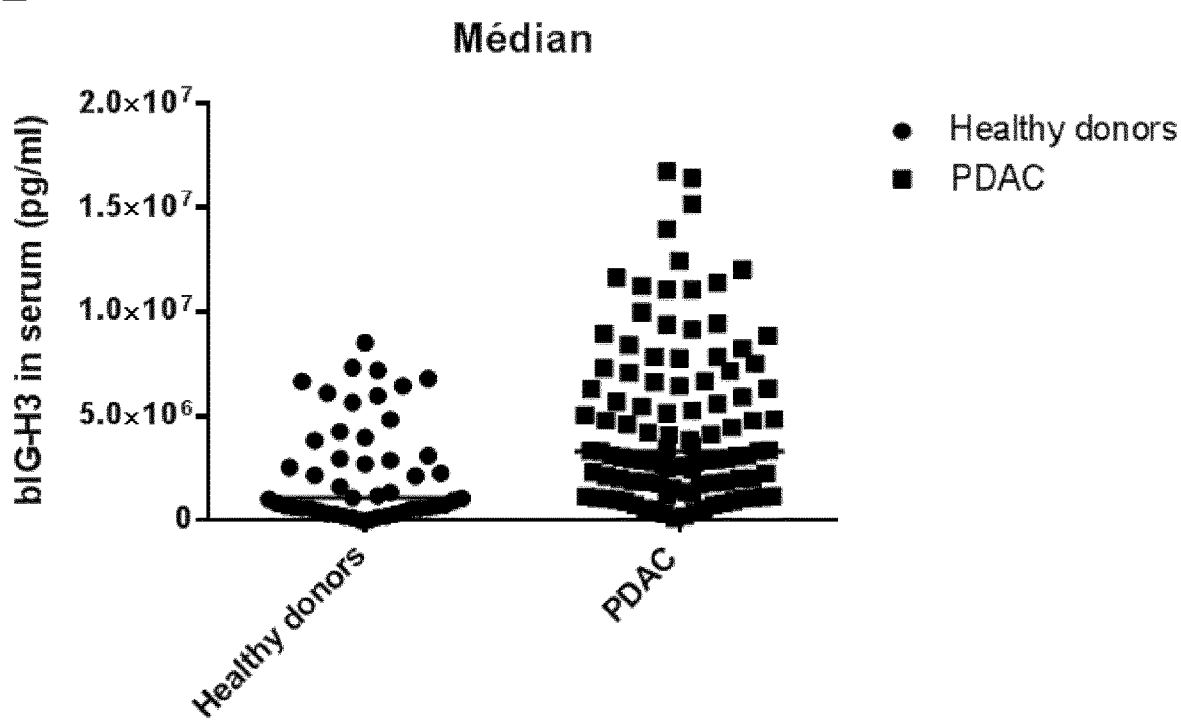
Figure 7A-B

EARLY AND NON INVASIVE METHOD FOR ASSESSING A SUBJECT'S RISK OF HAVING PANCREATIC DUCTAL ADENOCARCINOMA AND METHODS OF TREATMENT OF SUCH DISEASE

CROSS-REFERENCE TO RELATED APPLICATIONS

This application is a Rule 371 filing from PCT/EP2017/056150 filed Mar. 15, 2017, which claimed priority to European Application 16305276.4 filed Mar. 15, 2016.

FIELD OF THE INVENTION

The present invention relates to a method for preventing or treating a pancreatic ductal adenocarcinoma (PDAC). The present invention also relates to a diagnostic method of pancreatic ductal adenocarcinoma (PDAC). More particularly, the invention relates to a method for assessing a subject's risk of having pancreatic carcinoma, said method comprising the step of measuring the level of βig-h3 protein in a blood sample obtained from said subject wherein the level of βig-h3 is positively correlated with the risk of said subject of having a pancreatic ductal adenocarcinoma.

BACKGROUND OF THE INVENTION

Pancreatic Ductal Adenocarcinoma (PDAC) is one of the most lethal human malignancies and a major health problem. PDAC causes about 10,000 deaths per year in France and 230,000 in the worldwide (Jemal et al, 2003). The ratio of incidence/death is almost one indicating that virtually all patients presenting a PDAC will be killed by their disease. This is due to their short survival median that is about 6 months, the shortest of all tumors, because the treatments are relatively inefficient and because the disease was diagnosed at an advanced state. Despite considerable research efforts in the past decades, conventional treatment approaches, including surgery, radiation, chemotherapy, or combinations of these, had very limited impact. The prognosis is dismal with only 20% of patients alive one year after diagnosis (Jemal et al, 2003). Given this scenario, the search for new treatments that will counter PDAC progression and thereby increase patient life expectancy and quality of life has been given high priority.

An explanation for the low-efficiency, or high-resistance, to systemic therapies is that PDAC tumors are hypovascularised and very rich in stroma, representing from 15 to 90% of the tumor mass, which may form a barrier for drug delivery to the transformed cells.

The characteristics of PDAC are: (i) Incurable, as all patients will eventually relapse, underscoring a resistance of the disease to current treatment options. (ii) Very heterogeneous disease in terms of response to the—yet non-optimal—existing treatments. (iii) Drug resistance remains a major cause of treatment failure in PDAC and its inevitable fate due to the prolonged natural course of the disease and the repeated treatments, creating a relevant social and health problem. (iv) Robust and specific markers predictive of response to treatment are still lacking, though urgently needed in order to implement risk-adapted, personalized treatment and maximize clinical benefit while minimizing costs.

Gene profiling of whole PDAC tumors has been largely reported in the prior Art (see Abdollahi et al, 2007; Abiatari et al, 2009; Buchholz et al, 2005a; Buchholz et al, 2005b; Cavard et al, 2009; Crnogorac-Jurcevic et al, 2002; Gress et al, 1997; Ishikawa et al, 2005; Marcotte et al, 2012; Verma et al, 2012; Wang et al, 2013). However, the low reproducibility of those studies had discouraged the authors to go on exploring this direction.

The reasons for the failure of those approaches may be due to inappropriate tools, tools of insufficient quality, poor quality of the samples, or they may also be inherent to the pathology itself since PDAC tumors can contain from 15 to 90% of stroma tissue associated with variable areas of inflammation and necrosis.

Thus, and to inventor's knowledge, there are no available diagnostic biomarkers, for predicting the risk of individual subject to have/develop a pancreatic ductal adenocarcinoma (PDAC). In particular, a need remains for in vitro or ex vivo methods to diagnose the early stage of tumor onset of individual having PDAC.

A need also remains for methods and/or kits and/or solid supports, which are suitable for determining the diagnosis of an individual having PDAC, easily without invasive intratumor biopsy.

Therefore, there is a need for new biological markers of PDAC. In particular, biomarkers that would allow reliable diagnosis and monitoring of the early stages of the disease are highly desirable.

The purpose of the present invention is therefore to address this need by providing: i) a new reliable method for predicting whether a subject is affected by PDAC at an early stage of the disease onset and ii) a new therapeutical target for treating PDAC.

Inventors have recently shown that βig-h3 protein (Transforming growth factor beta-induced protein or TGFBIp), a secreted protein of the stroma, capable of binding to both extracellular matrix and cells, plays an important role to maintain islet tolerance and integrity against islet insult T cell cytotoxic attack in type 1 diabetes (Patry et al., 2015).

TGFBIp is an extracellular matrix protein expressed by human endothelial cells and platelets that induces sepsis through interaction with integrin αvβ5. Bae et al. shown that neutralizing anti-TGFBIp antibody inhibited the specific interactions between TGFBIp and integrin αvβ5, one of TGFBIp cognate receptors, (Bae et al., 2014). They demonstrated that treatments based on the use of a TGFBIp-neutralizing antibody can ameliorate the deleterious effects of sepsis. Furthermore, elevated expression of TGFBIp was previously described in several cancer cell lines and tumour biopsies, such as colon cancer cell lines and high grade advanced colon tumors (Ma et al., 2008) but also and pancreatic tissue (Turtoi et al., 2011). This expression was detected in tumour tissue (not at serum level) and it was associated with poor prognostic in well-advanced tumour (high grade advanced colon cancer in Ma et al 2008). Contrariwise, another study (Han et al. 2015) while the serum concentration of TGFBIp was assessed in patients suffering with various cancers, no significant association was ever observed in patients suffering of pancreatic cancer. Finally, none of these studies have explored the potential therapeutical targeting of TGFBIp in PDAC and especially as an immunological target in human.

SUMMARY OF THE INVENTION

A first object of the invention relates to a method for assessing a subject's risk of having or developing pancreatic ductal adenocarcinoma, said method comprising the step of measuring the level of βig-h3 protein in a blood sample obtained from said subject wherein the level of βig-h3 is positively correlated with the risk of said subject of having a pancreatic ductal adenocarcinoma.

A high level of βig-h3 is predictive of a high risk of having or developing a pancreatic ductal adenocarcinoma.

A low level of βig-h3 is predictive of a low risk of having a/or developing pancreatic ductal adenocarcinoma.

A second object of the invention relates to a method for monitoring the effect of a therapy for treating pancreatic ductal adenocarcinoma in a subject.

A third object of the invention also relates to βig-h3 antagonist for use in the prevention or treatment of a patient affected with a pancreatic ductal adenocarcinoma.

DETAILED DESCRIPTION OF THE INVENTION

Here the inventors investigated the correlation between βig-h3 serum levels and biological findings from PDAC patients. They found that surprisingly: 1) βig-h3 protein is highly produced by cancer associated fibroblasts (CAFs) in the tumor stroma in pancreatic neoplasia both in mice and in humans; 2) βig-h3 is expressed very early in tumorigenesis in pancreatic neoplastic lesions (PanIN1, PanIN2 and PanIN3 Stages) in a mouse model of PDAC predisposition as well as in PDAC patients 3) βig-h3 is secreted and can be detected in the serum of the mouse which developed pancreatic neoplastic lesions 4) βig-h3 acts directly on $CD8^+$ T cells by reducing their activation and cytotoxic properties 5) βig-h3 interacts with CD61 at the surface of CD8+ T cells 6) the use of neutralizing βig-h3 antibodies in PDAC mouse model, reduced tumor growth by enhancing $CD8^+$ T cell anti-tumoral response and 7) CD8+ T cells are mandatory for βig-h3 neutralization effect in vivo. These results show that βig-h3 contributes to the anti-tumoral $CD8^+$ T cell response blockade. Neutralizing βig-h3 which acts as a novel immunological check-point target in PDAC therefore allows to restore beneficial anti-tumor immunity in pancreatic cancer.

Diagnostic Methods According to the Invention

A first aspect of the invention consists of a method for assessing a subject's risk of having or developing ductal pancreatic adenocarcinoma (PDAC), said method comprising the step of measuring the level of βig-h3 protein in a blood sample obtained from said subject wherein the level of βig-h3 is positively correlated with the risk of said subject of having a pancreatic ductal adenocarcinoma.

A high level of βig-h3 is predictive of a high risk of having or developing a pancreatic ductal adenocarcinoma.

A low level of βig-h3 is predictive of a low risk of having or developing a pancreatic ductal adenocarcinoma.

Indeed, the inventors have surprisingly demonstrated that βig-h3, known until now to be an extracellular matrix protein expressed by human endothelial cells or various tumour cells, is a circulating protein present in blood.

In one embodiment, the blood sample to be used in the methods according to the invention is a whole blood sample, a serum sample, or a plasma sample. In a preferred embodiment, the blood sample is a serum sample.

In a particular embodiment, methods of the invention are suitable for assessing a subject's risk of having or developing pancreatic carcinoma (PDAC) at an early stage: for instance when occur pancreatic neoplastic lesions (IPMNs (Intra-Pancreatic Mucinous Neoplasia), MCNs (Mucinous Cystics Neoplasia), PanIN1, PanIN2 and PanIN3 Stages).

As defined herein the term "βig-h3" or (βig-h3) also known as "Transforming growth factor β-induced protein" or "TGFBIp" or "TGFBi" is an extracellular matrix protein expressed by human endothelial cells and platelets that in humans is encoded by the TGFBI gene. This gene encodes an RGD-containing protein that binds to type I, II and IV collagens. The RGD motif is found in many extracellular matrix proteins modulating cell adhesion and serves as a ligand recognition sequence for several integrins. This protein plays a role in cell-collagen interactions and may be involved in endochondrial bone formation in cartilage. The protein is induced by transforming growth factor-beta and acts to inhibit cell adhesion. Mutations of the gene cause several forms of corneal dystrophies (Munier et al 1997). One example of wild-type βig-h3 human amino acid sequence is provided in SEQ ID NO:1 (NCBI Reference Sequence: NP_000349). One example of nucleotide sequence encoding wild-type βig-h3 amino acid sequence of SEQ ID NO:1 is provided in SEQ ID NO:2 (NCBI Reference Sequence: NM_000358).

In one embodiment of the methods defined above, one or more biological markers are quantified together with βig-h3.

As used herein, a "biological marker" encompasses any detectable product that is synthesized upon the expression of a specific gene, and thus includes gene-specific mRNA, cDNA and protein.

The various biological markers names specified herein correspond to their internationally recognized acronyms that are usable to get access to their complete amino acid and nucleic acid sequences, including their complementary DNA (cDNA) and genomic DNA sequences. Illustratively, the corresponding amino acid and nucleic acid sequences of each of the biological markers specified herein may be retrieved, on the basis of their acronym names, that are also termed herein "gene symbols", in the GenBank or EMBL sequence databases. All gene symbols listed in the present specification correspond to the GenBank nomenclature. Their DNA (cDNA and gDNA) sequences, as well as their amino acid sequences are thus fully available to the one skilled in the art from the GenBank database.

Of course variant sequences of the biological markers may be employed in the context of the present invention, those including but not limited to functional homologues, paralogues or orthologues of such sequences.

As used herein, the term "subject" denotes a mammal, such as a rodent, a feline, a canine, and a primate. Preferably, a subject according to the invention is a human.

The term "pancreatic ductal adenocarcinoma" refers to or describes the pathological condition in mammals that is typically characterized by unregulated pancreas cell growth. More precisely, Pancreatic ductal adenocarcinoma (PDAC) is a malignant tumor characterized by rapid progression that affects the exocrine compartment. PDAC is associated with an abundant stromal reaction, which accounts for up to 90% of the tumor volume. Since few years, the contribution of this massive stroma has emerged as a novel actor and contributor of pancreatic tumor initiation and progression.

The level of the βig-h3 may be determined by using standard electrophoretic and immunodiagnostic techniques, including immunoassays such as competition, direct reaction such as immunohistochemistry, or sandwich type assays. Such assays include, but are not limited to, Western blots; agglutination tests; enzyme-labelled and mediated immunoassays, such as ELISAs; biotin/avidin type assays; radioimmunoassays; immunoelectrophoresis; immunoprecipitation, etc. The reactions generally include revealing labels such as fluorescent, chemiluminescent, radioactive, enzymatic labels or dye molecules, or other methods for detecting the formation of a complex between the antigen and the antibody or antibodies reacted therewith.

For example, determination of the βig-h3 level can be performed by a variety of techniques and method any well known method in the art: RIA kits (DiaSorin; IDS, Diasource) Elisa kits (Thermo Fisher, EHTGFBI, R&D DY2935, IDS (manual) IDS (adapted on open analyzers) Immunochemiluminescent automated methods (DiaSorin Liaison, Roche Elecsys family, IDS iSYS) (Janssen et al., 2012).

In a particular embodiment, the methods of the invention comprise contacting the blood sample with a binding partner.

As used therein, binding partner refers to a molecule capable of selectively interacting with βig-h3.

The binding partner may be generally an antibody that may be polyclonal or monoclonal, preferably monoclonal. Polyclonal antibodies directed against βig-h3 can be raised according to known methods by administering the appropriate antigen or epitope to a host animal selected, e.g., from pigs, cows, horses, rabbits, goats, sheep, and mice, among others. Various adjuvants known in the art can be used to enhance antibody production. Although antibodies useful in practicing the invention can be polyclonal, monoclonal antibodies are preferred. Monoclonal antibodies against βig-h3 can be prepared and isolated using any technique that provides for the production of antibody molecules by continuous cell lines in culture. Techniques for production and isolation include but are not limited to the hybridoma technique originally described by Kohler et al. Nature. 1975; 256(5517):495-7; the human B-cell hybridoma technique (Cote et al Proc Natl Acad Sci USA. 1983; 80(7):2026-30); and the EBV-hybridoma technique (Cole et al., 1985, in "Monoclonal Antibodies and Cancer Therapy," Alan R. Liss, Inc. pp. 77-96). Alternatively, techniques described for the production of single chain antibodies (see e.g. U.S. Pat. No. 4,946,778) can be adapted to produce anti-βig-h3, single chain antibodies. Antibodies useful in practicing the present invention also include anti-βig-h3 including but not limited to F(ab')2 fragments, which can be generated by pepsin digestion of an intact antibody molecule, and Fab fragments, which can be generated by reducing the disulfide bridges of the F(ab')2 fragments. Alternatively, Fab and/or scFv expression libraries can be constructed to allow rapid identification of fragments having the desired specificity to βig-h3. For example, phage display of antibodies may be used. In such a method, single-chain Fv (scFv) or Fab fragments are expressed on the surface of a suitable bacteriophage, e. g., M13. Briefly, spleen cells of a suitable host, e. g., mouse, that has been immunized with a protein are removed. The coding regions of the VL and VH chains are obtained from those cells that are producing the desired antibody against the protein. These coding regions are then fused to a terminus of a phage sequence. Once the phage is inserted into a suitable carrier, e. g., bacteria, the phage displays the antibody fragment. Phage display of antibodies may also be provided by combinatorial methods known to those skilled in the art. Antibody fragments displayed by a phage may then be used as part of an immunoassay.

In another embodiment, the binding partner may be an aptamer. Aptamers are a class of molecule that represents an alternative to antibodies in term of molecular recognition. Aptamers are oligonucleotide or oligopeptide sequences with the capacity to recognize virtually any class of target molecules with high affinity and specificity. Such ligands may be isolated through Systematic Evolution of Ligands by EXponential enrichment (SELEX) of a random sequence library, as described in Tuerk et al. (1990) Science, 249, 505-510. The random sequence library is obtainable by combinatorial chemical synthesis of DNA. In this library, each member is a linear oligomer, eventually chemically modified, of a unique sequence. Possible modifications, uses and advantages of this class of molecules have been reviewed in Jayasena 1999. Peptide aptamers consist of conformationally constrained antibody variable regions displayed by a platform protein, such as E. coli Thioredoxin A, that are selected from combinatorial libraries by two hybrid methods (Colas et al. (1996) Nature, 380, 548-50).

The binding partners of the invention such as antibodies or aptamers, may be labeled with a detectable molecule or substance, such as a fluorescent molecule, a radioactive molecule or any others labels known in the art. Labels are known in the art that generally provide (either directly or indirectly) a signal.

As used herein, the term "labeled", with regard to the binding partner, is intended to encompass direct labeling of the antibody or aptamer by coupling (i.e., physically linking) a detectable substance, such as a radioactive agent or a fluorophore (e.g. fluorescein isothiocyanate (FITC) or phycoerythrin (PE) or Indocyanine (Cy5)) to the antibody or aptamer, as well as indirect labeling of the probe or antibody by reactivity with a detectable substance. An antibody or aptamer of the invention may be labeled with a radioactive molecule by any method known in the art. For example radioactive molecules include but are not limited radioactive atom for scintigraphic studies such as I123, I124, In111, Re186, Re188.

The aforementioned assays generally involve the bounding of the binding partner (ie. antibody or aptamer) in a solid support. Solid supports which can be used in the practice of the invention include substrates such as nitrocellulose (e. g., in membrane or microtiter well form); polyvinylchloride (e. g., sheets or microtiter wells); polystyrene latex (e.g., beads or microtiter plates); polyvinylidine fluoride; diazotized paper; nylon membranes; activated beads, magnetically responsive beads, and the like. More particularly, an ELISA method can be used, wherein the wells of a microtiter plate are coated with a set of antibodies against βig-h3. A body fluid sample containing or suspected of containing βig-h3 is then added to the coated wells. After a period of incubation sufficient to allow the formation of binding partner-βig-h3 complexes, the plate(s) can be washed to remove unbound material and a labeled secondary binding molecule added. The secondary binding molecule is allowed to react with any captured sample marker protein, the plate washed and the presence of the secondary binding molecule detected using methods well known in the art.

As the binding partner, the secondary binding molecule may be labeled.

Different immunoassays, such as radioimmunoassay or ELISA, have been described in the art.

Measuring the level of βig-h3 with or without immunoassay-based methods may also include separation of the proteins: centrifugation based on the protein's molecular weight; electrophoresis based on mass and charge; HPLC based on hydrophobicity; size exclusion chromatography based on size; and solid-phase affinity based on the protein's affinity for the particular solid-phase that is use. Once separated, βig-h3 may be identified based on the known "separation profile" e. g., retention time, for that protein and measured using standard techniques. Alternatively, the separated proteins may be detected and measured by, for example, a mass spectrometer.

In a preferred embodiment, the method for measuring the level of βig-h3 comprises the step of contacting the blood sample with a binding partner capable of selectively interacting with βig-h3 to allow formation of a binding partner-βig-h3 complex.

In more preferred embodiment, the method according to the invention comprises further the steps of separating any unbound material of the blood sample from the binding partner-βig-h3 complex, contacting the binding partner-βig-h3 complex with a labelled secondary binding molecule, separating any unbound secondary binding molecule from secondary binding molecule-βig-h3 complexes and measuring the level of the secondary binding molecule of the secondary binding molecule-βig-h3 complexes.

Typically, a high or a low level of βig-h3 is intended by comparison to a control reference value.

Said reference control values may be determined in regard to the level of βig-h3 present in blood samples taken from one or more healthy subject or to the βig-h3 distribution in a control population.

In one embodiment, the method according to the present invention comprises the step of comparing said level of βig-h3 to a control reference value wherein a high level of βig-h3 compared to said control reference value is predictive of a high risk of having a pancreatic ductal adenocarcinoma and a low level of βig-h3 compared to said control reference value is predictive of a low risk of having a pancreatic ductal adenocarcinoma.

The control reference value may depend on various parameters such as the method used to measure the level of βig-h3 or the gender of the subject.

Typically, for a level of βig-h3 in a serum sample measured using a competitive immunoassay with a polyclonal antibody raised against human βig-h3, a level of βig-h3 superior to 5 μg/ml, is predictive of a high risk of having a pancreatic ductal adenocarcinoma and a level of βig-h3 lower than 5 μg/ml is predictive of a low risk of having a pancreatic ductal adenocarcinoma.

Control reference values are easily determinable by the one skilled in the art, by using the same techniques as for determining the level of βig-h3 in blood samples previously collected from the patient under testing.

A "control reference value" can be a "threshold value" or a "cut-off value". Typically, a "threshold value" or "cut-off value" can be determined experimentally, empirically, or theoretically. A threshold value can also be arbitrarily selected based upon the existing experimental and/or clinical conditions, as would be recognized by a person of ordinary skilled in the art. The threshold value has to be determined in order to obtain the optimal sensitivity and specificity according to the function of the test and the benefit/risk balance (clinical consequences of false positive and false negative). Typically, the optimal sensitivity and specificity (and so the threshold value) can be determined using a Receiver Operating Characteristic (ROC) curve based on experimental data. Preferably, the person skilled in the art may compare the βig-h3 levels (obtained according to the method of the invention) with a defined threshold value. In one embodiment of the present invention, the threshold value is derived from the βig-h3 level (or ratio, or score) determined in a blood sample derived from one or more subjects who are responders to pancreatic ductal adenocarcinoma treatment. In one embodiment of the present invention, the threshold value may also be derived from βig-h3 level (or ratio, or score) determined in a blood sample derived from one or more subjects who are not affected with pancreatic ductal adenocarcinoma. Furthermore, retrospective measurement of the βig-h3 levels (or ratio, or scores) in properly banked historical subject samples may be used in establishing these threshold values.

"Risk" in the context of the present invention, relates to the probability that an event will occur over a specific time period, as in the conversion to pancreatic ductal adenocarcinoma (PDAC), and can mean a subject's "absolute" risk or "relative" risk. Absolute risk can be measured with reference to either actual observation post-measurement for the relevant time cohort, or with reference to index values developed from statistically valid historical cohorts that have been followed for the relevant time period. Relative risk refers to the ratio of absolute risks of a subject compared either to the absolute risks of low risk cohorts or an average population risk, which can vary by how clinical risk factors are assessed. Odds ratios, the proportion of positive events to negative events for a given test result, are also commonly used (odds are according to the formula p/(1−p) where p is the probability of event and (1−p) is the probability of no event) to no conversion. Alternative continuous measures, which may be assessed in the context of the present invention, include time to AMC and/or congenital peripheral neuropathy disease conversion and therapeutic AMC and/or congenital peripheral neuropathy disease conversion risk reduction ratios.

"Risk evaluation," or "evaluation of risk" in the context of the present invention encompasses making a prediction of the probability, odds, or likelihood that an event or disease state may occur, the rate of occurrence of the event or conversion from one disease state to another, i.e., from a normal condition to a PDAC condition or to one at risk of developing a PDAC. Risk evaluation can also comprise prediction of future clinical parameters, traditional laboratory risk factor values, or other indices of PDAC, such as cellular population determination in peripheral tissues, in serum or other fluid, either in absolute or relative terms in reference to a previously measured population. The methods of the present invention may be used to make continuous or categorical measurements of the risk of conversion to PDAC, thus diagnosing and defining the risk spectrum of a category of subjects defined as being at risk for a PDAC. In the categorical scenario, the invention can be used to discriminate between normal and other subject cohorts at higher risk for PADC. In other embodiments, the present invention may be used so as to help to discriminate those having PDAC from normal.

The invention also relates to the use of βig-h3 as a blood biomarker of PDAC, especially at early stage. According the present invention, early stage of PDAC means for instance when occurs pancreatic neoplastic lesions (PanIN1, PanIN2 and PanIN3 Stages).

Monitoring Anti-Pancreatic Cancer Treatments

Monitoring the influence of agents (e.g., drug compounds) on the level of expression of one or more tissue-specific biological markers of the invention can be applied for monitoring the malignant potency of the treated pancreatic ductal adenocarcinoma of the patient with time. For example, the effectiveness of an agent to affect βig-h3 expression can be monitored during treatments of subjects receiving anti-cancer, and especially chemotherapy treatments.

Accordingly, a second object of the invention also relates to method for monitoring the effect of a therapy for treating pancreatic ductal adenocarcinoma in a subject comprising the step of measuring the level of βig-h3 in a first blood sample obtained from said subject at t1 and measuring the level of βig-h3 in a second blood sample obtained from said subject at t2 wherein when t1 is prior to therapy, t2 is during or following therapy, and when t1 is during therapy, t2 is later during therapy or following therapy, and wherein a decrease in the level of βig-h3 in the second sample as compared to the level of βig-h3 in the first sample is indicative of a positive effect of the therapy on pancreatic ductal adenocarcinoma in the treated subject.

In another embodiment, the present invention provides a method for monitoring the effectiveness of treatment of a subject with an agent (e.g., an agonist, antagonist, peptidomimetic, protein, peptide, nucleic acid, small molecule, or other drug candidate) comprising the steps of (i) obtaining a pre-administration blood sample from a subject prior to administration of the agent; (ii) detecting the βig-h3 blood level; (iii) obtaining one or more post-administration samples from the subject; (iv) detecting βig-h3 blood level in the post-administration samples; (v) comparing βig-h3 level in the pre-administration sample with the level of expression in the post-administration sample or samples; and (vi) altering the administration of the agent to the subject accordingly. For example, increased βig-h3 blood level during the course of treatment may indicate ineffective dosage and the desirability of increasing the dosage, or indicative to the necessity to change the treatment. Conversely, decreased βig-h3 blood may indicate efficacious treatment and no need to change dosage.

In a specific embodiment, the therapy for treating pancreatic ductal adenocarcinoma is selected from the group consisting of chemotherapy treatment and/or a βig-h3 antagonist.

Because repeated collection of biological samples from the cancer-bearing patient are needed for performing the monitoring method described above, then preferred biological samples is blood samples susceptible to contain (i) cells originating from the patient's pancreatic ductal adenocarcinoma tissue, or (ii) specific marker expression products synthesized by cells originating from the patients pancreatic ductal adenocarcinoma tissue, including nucleic acids and proteins.

Therapeutic Methods and Uses

The present invention provides methods and compositions (such as pharmaceutical compositions) for preventing or treating a pancreatic ductal adenocarcinoma. The present invention also provides methods and compositions for inhibiting or preventing pancreatic ductal adenocarcinoma.

In the context of the invention, the term "treatment or prevention" means reversing, alleviating, inhibiting the progress of, or preventing the disorder or condition to which such term applies, or one or more symptoms of such disorder or condition. In particular, the treatment of the disorder may consist in reducing the number of malignant cells. Most preferably, such treatment leads to the complete depletion of the malignant cells.

Preferably, the individual to be treated is a human or non-human mammal (such as a rodent (mouse, rat), a feline, a canine, or a primate) affected or likely to be affected with cancer. Preferably, the individual is a human.

According to a first aspect, the present invention relates to a βig-h3 antagonist for use in the prevention or the treatment of a patient affected with a pancreatic ductal adenocarcinoma.

An "βig-h3 antagonist" refers to a molecule (natural or synthetic) capable of neutralizing, blocking, inhibiting, abrogating, reducing or interfering with the activities of βig-h3 including, for example, reduction or blocking the interaction between βig-h3 and αVβ3 integrin. βig-h3 antagonists include antibodies and antigen-binding fragments thereof, proteins, peptides, glycoproteins, glycopeptides, glycolipids, polysaccharides, oligosaccharides, nucleic acids, bioorganic molecules, peptidomimetics, pharmacological agents and their metabolites, transcriptional and translation control sequences, and the like. Antagonists also include, antagonist variants of the protein, siRNA molecules directed to a protein, antisense molecules directed to a protein, aptamers, and ribozymes against a protein. For instance, the βig-h3 antagonist may be a molecule that binds to βig-h3 and neutralizes, blocks, inhibits, abrogates, reduces or interferes with the biological activity of βig-h3 (such as inducing tumor cell growth). More particularly, the βig-h3 antagonist according to the invention is an anti-βig-h3 antibody.

By "biological activity" of a βig-h3 is meant inducing tumor cell growth and inhibiting CD8$^+$ T cell activation (blocking the anti-tumoral response).

Tests for determining the capacity of a compound to be βig-h3 antagonist are well known to the person skilled in the art. In a preferred embodiment, the antagonist specifically binds to βig-h3 in a sufficient manner to inhibit the biological activity of βig-h3. Binding to βig-h3 and inhibition of the biological activity of βig-h3 may be determined by any competing assays well known in the art. For example, the assay may consist in determining the ability of the agent to be tested as βig-h3 antagonist to bind to βig-h3. The binding ability is reflected by the Kd measurement. The term "KD", as used herein, is intended to refer to the dissociation constant, which is obtained from the ratio of Kd to Ka (i.e. Kd/Ka) and is expressed as a molar concentration (M). KD values for binding biomolecules can be determined using methods well established in the art. In specific embodiments, an antagonist that "specifically binds to βig-h3" is intended to refer to an inhibitor that binds to human βig-h3 polypeptide with a KD of 1 µM or less, 100 nM or less, 10 nM or less, or 3 nM or less. Then a competitive assay may be settled to determine the ability of the agent to inhibit biological activity of βig-h3. The functional assays may be envisaged such evaluating the ability to inhibit a) induction of tumor cell growth and/or b) inhibition of CD8$^+$ T cell activation (see example with blocking βig-h3 antibody and FIGS. 2 and 3).

The skilled in the art can easily determine whether a βig-h3 antagonist neutralizes, blocks, inhibits, abrogates, reduces or interferes with a biological activity of βig-h3. To check whether the βig-h3 antagonist bind to βig-h3 and/or is able to inhibit tumor cell growth and/or blocking the inhibiting CD8$^+$ T cell activation in the same way than the initially characterized blocking βig-h3 antibody and/or binding assay and/or a cell proliferation assay and/or or a inhibiting CD8+ T cell activation assay may be performed with each antagonist. For instance inhibiting CD8$^+$ T cell activation can be assessed by detecting cells expressing activation markers with antibody anti-CD69 and anti-CD44 (CD8$^+$ T cells) as described in the Examples section (FIG. 2) and cell proliferation assay can be measured by CFSE-proliferation assay.

Accordingly, the βig-h3 antagonist may be a molecule that binds to βig-h3 selected from the group consisting of antibodies, aptamers, and polypeptides.

The skilled in the art can easily determine whether a βig-h3 antagonist neutralizes, blocks, inhibits, abrogates, reduces or interferes with a biological activity of βig-h3: (i)

binding to βig-h3 and/or (ii) inducing tumor cell growth and/or (iii) inhibiting CD8+ T cell activation.

Accordingly, in a specific embodiment the βig-h3 antagonist directly binding to βig-h3 and inhibits the inhibition of CD8+ T cell activation (or restore CD8+ T cell activation).

The present invention also relates to a βig-h3 antagonist for use in a method to activate the anti-tumoral CD8+T cell response of a patient affected with a cancer.

The terms "cancer" and "tumors" refer to or describe the pathological condition in mammals that is typically characterized by unregulated cell growth. More precisely, in the use of the invention, diseases, namely tumors that express/secrete βig-h3 are most likely to respond to the βig-h3 antagonist after the restoration of CD8+ T cell activation. In particular, the cancer may be associated with a solid tumor or lymphoma/leukemia (from hematopoietic cell). Examples of cancers that are associated with solid tumor formation include breast cancer, uterine/cervical cancer, oesophageal cancer, pancreatic cancer, colon cancer, colorectal cancer, kidney cancer, ovarian cancer, prostate cancer, head and neck cancer, non-small cell lung cancer stomach cancer, tumors of mesenchymal origin (i.e; fibrosarcoma and rhabdomyoscarcoma) tumors of the central and peripheral nervous system (i.e; including astrocytoma, neuroblastoma, glioma, glioblatoma) thyroid cancer.

Preferably the solid tumor is selected from the group consisting of pancreatic cancer eosophage squamous cell carcinoma (Ozawa et al, 2014), gastric and hepatic carcinoma (Han et al, 2015), colon cancer (Ma et al, 2008), melanoma (Lauden et al, 2014).

More preferably the pancreatic cancer is pancreatic ductal adenocarcinoma.

The terms "anti-tumoral CD8+T cell response" means the natural ability of the CD8+T cell to lyse cancer cells (Robbins and Kawakami, 1996, Romero, 1996)

Antibody

In another embodiment, the βig-h3 antagonist is an antibody (the term including antibody fragment or portion) that can block the interaction of βig-h3 with αVβ3 integrin.

In preferred embodiment, the βig-h3 antagonist may consist in an antibody directed against the βig-h3, in such a way that said antibody impairs the binding of a βig-h3 to αVβ3 integrin ("neutralizing antibody").

Then, for this invention, neutralizing antibody of βig-h3 are selected as above described for their capacity to (i) bind to βig-h3 and/or (ii) inhibiting tumor cell growth and/or (iii) blocking the inhibiting CD8⁺ T cell activation.

In one embodiment of the antibodies or portions thereof described herein, the antibody is a monoclonal antibody. In one embodiment of the antibodies or portions thereof described herein, the antibody is a polyclonal antibody. In one embodiment of the antibodies or portions thereof described herein, the antibody is a humanized antibody. In one embodiment of the antibodies or portions thereof described herein, the antibody is a chimeric antibody. In one embodiment of the antibodies or portions thereof described herein, the portion of the antibody comprises a light chain of the antibody. In one embodiment of the antibodies or portions thereof described herein, the portion of the antibody comprises a heavy chain of the antibody. In one embodiment of the antibodies or portions thereof described herein, the portion of the antibody comprises a Fab portion of the antibody. In one embodiment of the antibodies or portions thereof described herein, the portion of the antibody comprises a F(ab')2 portion of the antibody. In one embodiment of the antibodies or portions thereof described herein, the portion of the antibody comprises a Fc portion of the antibody. In one embodiment of the antibodies or portions thereof described herein, the portion of the antibody comprises a Fv portion of the antibody. In one embodiment of the antibodies or portions thereof described herein, the portion of the antibody comprises a variable domain of the antibody. In one embodiment of the antibodies or portions thereof described herein, the portion of the antibody comprises one or more CDR domains of the antibody.

As used herein, "antibody" includes both naturally occurring and non-naturally occurring antibodies. Specifically, "antibody" includes polyclonal and monoclonal antibodies, and monovalent and divalent fragments thereof. Furthermore, "antibody" includes chimeric antibodies, wholly synthetic antibodies, single chain antibodies, and fragments thereof. The antibody may be a human or nonhuman antibody. A nonhuman antibody may be humanized by recombinant methods to reduce its immunogenicity in man.

Antibodies are prepared according to conventional methodology. Monoclonal antibodies may be generated using the method of Kohler and Milstein (Nature, 256:495, 1975). To prepare monoclonal antibodies useful in the invention, a mouse or other appropriate host animal is immunized at suitable intervals (e.g., twice-weekly, weekly, twice-monthly or monthly) with antigenic forms of βig-h3. The animal may be administered a final "boost" of antigen within one week of sacrifice. It is often desirable to use an immunologic adjuvant during immunization. Suitable immunologic adjuvants include Freund's complete adjuvant, Freund's incomplete adjuvant, alum, Ribi adjuvant, Hunter's Titermax, saponin adjuvants such as QS21 or Quil A, or CpG-containing immunostimulatory oligonucleotides. Other suitable adjuvants are well-known in the field. The animals may be immunized by subcutaneous, intraperitoneal, intramuscular, intravenous, intranasal or other routes. A given animal may be immunized with multiple forms of the antigen by multiple routes.

Briefly, the recombinant βig-h3 may be provided by expression with recombinant cell lines. Recombinant form of βig-h3 may be provided using any previously described method. Following the immunization regimen, lymphocytes are isolated from the spleen, lymph node or other organ of the animal and fused with a suitable myeloma cell line using an agent such as polyethylene glycol to form a hydridoma. Following fusion, cells are placed in media permissive for growth of hybridomas but not the fusion partners using standard methods, as described (Coding, Monoclonal Antibodies: Principles and Practice: Production and Application of Monoclonal Antibodies in Cell Biology, Biochemistry and Immunology, 3rd edition, Academic Press, New York, 1996). Following culture of the hybridomas, cell supernatants are analyzed for the presence of antibodies of the desired specificity, i.e., that selectively bind the antigen. Suitable analytical techniques include ELISA, flow cytometry, immunoprecipitation, and western blotting. Other screening techniques are well-known in the field. Preferred techniques are those that confirm binding of antibodies to conformationally intact, natively folded antigen, such as non-denaturing ELISA, flow cytometry, and immunoprecipitation.

Significantly, as is well-known in the art, only a small portion of an antibody molecule, the paratope, is involved in the binding of the antibody to its epitope (see, in general, Clark, W. R. (1986) *The Experimental Foundations of Modern Immunology* Wiley & Sons, Inc., New York; Roitt, I. (1991) *Essential Immunology*, 7th Ed., Blackwell Scientific Publications, Oxford). The Fc' and Fc regions, for example, are effectors of the complement cascade but are not involved in antigen binding. An antibody from which the pFc' region has been enzymatically cleaved, or which has been produced without the pFc' region, designated an F(ab')2 fragment, retains both of the antigen binding sites of an intact antibody. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd. The Fd fragments are the major determinant of antibody specificity (a single Fd fragment may be associated with up to ten different light chains without altering antibody specificity) and Fd fragments retain epitope-binding ability in isolation.

Within the antigen-binding portion of an antibody, as is well-known in the art, there are complementarity determining regions (CDRs), which directly interact with the epitope of the antigen, and framework regions (FRs), which maintain the tertiary structure of the paratope (see, in general, Clark, 1986; Roitt, 1991). In both the heavy chain Fd fragment and the light chain of IgG immunoglobulins, there are four framework regions (FR1 through FR4) separated respectively by three complementarity determining regions (CDR1 through CDRS). The CDRs, and in particular the CDRS regions, and more particularly the heavy chain CDRS, are largely responsible for antibody specificity.

It is now well-established in the art that the non CDR regions of a mammalian antibody may be replaced with similar regions of conspecific or heterospecific antibodies while retaining the epitopic specificity of the original antibody. This is most clearly manifested in the development and use of "humanized" antibodies in which non-human CDRs are covalently joined to human FR and/or Fc/pFc' regions to produce a functional antibody.

This invention provides in certain embodiments compositions and methods that include humanized forms of antibodies. As used herein, "humanized" describes antibodies wherein some, most or all of the amino acids outside the CDR regions are replaced with corresponding amino acids derived from human immunoglobulin molecules. Methods of humanization include, but are not limited to, those described in U.S. Pat. Nos. 4,816,567, 5,225,539, 5,585,089, 5,693,761, 5,693,762 and 5,859,205, which are hereby incorporated by reference. The above U.S. Pat. Nos. 5,585,089 and 5,693,761, and WO 90/07861 also propose four possible criteria which may used in designing the humanized antibodies. The first proposal was that for an acceptor, use a framework from a particular human immunoglobulin that is unusually homologous to the donor immunoglobulin to be humanized, or use a consensus framework from many human antibodies. The second proposal was that if an amino acid in the framework of the human immunoglobulin is unusual and the donor amino acid at that position is typical for human sequences, then the donor amino acid rather than the acceptor may be selected. The third proposal was that in the positions immediately adjacent to the 3 CDRs in the humanized immunoglobulin chain, the donor amino acid rather than the acceptor amino acid may be selected. The fourth proposal was to use the donor amino acid reside at the framework positions at which the amino acid is predicted to have a side chain atom within 3A of the CDRs in a three dimensional model of the antibody and is predicted to be capable of interacting with the CDRs. The above methods are merely illustrative of some of the methods that one skilled in the art could employ to make humanized antibodies. One of ordinary skill in the art will be familiar with other methods for antibody humanization.

In one embodiment of the humanized forms of the antibodies, some, most or all of the amino acids outside the CDR regions have been replaced with amino acids from human immunoglobulin molecules but where some, most or all amino acids within one or more CDR regions are unchanged. Small additions, deletions, insertions, substitutions or modifications of amino acids are permissible as long as they would not abrogate the ability of the antibody to bind a given antigen. Suitable human immunoglobulin molecules would include IgG1, IgG2, IgG3, IgG4, IgA and IgM molecules. A "humanized" antibody retains a similar antigenic specificity as the original antibody. However, using certain methods of humanization, the affinity and/or specificity of binding of the antibody may be increased using methods of "directed evolution", as described by Wu et al., /. Mol. Biol. 294:151, 1999, the contents of which are incorporated herein by reference.

Fully human monoclonal antibodies also can be prepared by immunizing mice transgenic for large portions of human immunoglobulin heavy and light chain loci. See, e.g., U.S. Pat. Nos. 5,591,669, 5,598,369, 5,545,806, 5,545,807, 6,150,584, and references cited therein, the contents of which are incorporated herein by reference. These animals have been genetically modified such that there is a functional deletion in the production of endogenous (e.g., murine) antibodies. The animals are further modified to contain all or a portion of the human germ-line immunoglobulin gene locus such that immunization of these animals will result in the production of fully human antibodies to the antigen of interest. Following immunization of these mice (e.g., XenoMouse (Abgenix), HuMAb mice (Medarex/GenPharm)), monoclonal antibodies can be prepared according to standard hybridoma technology. These monoclonal antibodies will have human immunoglobulin amino acid sequences and therefore will not provoke human anti-mouse antibody (KAMA) responses when administered to humans.

In vitro methods also exist for producing human antibodies. These include phage display technology (U.S. Pat. Nos. 5,565,332 and 5,573,905) and in vitro stimulation of human B cells (U.S. Pat. Nos. 5,229,275 and 5,567,610). The contents of these patents are incorporated herein by reference.

Thus, as will be apparent to one of ordinary skill in the art, the present invention also provides for F(ab') 2 Fab, Fv and Fd fragments; chimeric antibodies in which the Fc and/or FR and/or CDR1 and/or CDR2 and/or light chain CDR3 regions have been replaced by homologous human or non-human sequences; chimeric F(ab')2 fragment antibodies in which the FR and/or CDR1 and/or CDR2 and/or light chain CDR3 regions have been replaced by homologous human or non-human sequences; chimeric Fab fragment antibodies in which the FR and/or CDR1 and/or CDR2 and/or light chain CDR3 regions have been replaced by homologous human or non-human sequences; and chimeric Fd fragment antibodies in which the FR and/or CDR1 and/or CDR2 regions have been replaced by homologous human or non-human sequences. The present invention also includes so-called single chain antibodies.

The various antibody molecules and fragments may derive from any of the commonly known immunoglobulin classes, including but not limited to IgA, secretory IgA, IgE, IgG and IgM. IgG subclasses are also well known to those in the art and include but are not limited to human IgG1, IgG2, IgG3 and IgG4.

In another embodiment, the antibody according to the invention is a single domain antibody. The term "single domain antibody" (sdAb) or "VHH" refers to the single heavy chain variable domain of antibodies of the type that can be found in Camelid mammals which are naturally devoid of light chains. Such VHH are also called "Nanobody®". According to the invention, sdAb can particularly be llama sdAb.

Example of neutralizing anti-βig-h3 antibody is disclosed, for example, in Bae J S et al Acta Physiol 2014, 212, 306-315. The skilled artisan canuse routine technologies to use the antigen-binding sequences of these antibodies (e.g., the CDRs) and generate humanized antibodies for treatment of PDAC as disclosed herein.

Aptamer

In another embodiment, the βig-h3 antagonist is an aptamer directed against βig-h3. Aptamers are a class of molecule that represents an alternative to antibodies in term of molecular recognition. Aptamers are oligonucleotide or oligopeptide sequences with the capacity to recognize virtually any class of target molecules with high affinity and specificity. Such ligands may be isolated through Systematic Evolution of Ligands by EXponential enrichment (SELEX) of a random sequence library, as described in Tuerk C. and Gold L., 1990. The random sequence library is obtainable by combinatorial chemical synthesis of DNA. In this library, each member is a linear oligomer, eventually chemically modified, of a unique sequence. Possible modifications, uses and advantages of this class of molecules have been reviewed in Jayasena S. D., 1999. Peptide aptamers consists of a conformationally constrained antibody variable region displayed by a platform protein, such as *E. coli* Thioredoxin A that are selected from combinatorial libraries by two hybrid methods (Colas et al., 1996).

Then, for this invention, neutralizing aptamers of βig-h3 are selected as above described for their capacity to (i) bind to βig-h3 and/or (ii) inhibit tumor cell growth and/or (iii) blocking the inhibiting CD8+ T cell activation.

Inhibitor of βig-h3 Gene Expression

In still another embodiment, the βig-h3 antagonist is an inhibitor of βig-h3 gene expression. An "inhibitor of expression" refers to a natural or synthetic compound that has a biological effect to inhibit the expression of a gene. Therefore, an "inhibitor of βig-h3 gene expression" denotes a natural or synthetic compound that has a biological effect to inhibit the expression of βig-h3 gene.

In a preferred embodiment of the invention, said inhibitor of βig-h3 gene expression is a siRNA, an antisense oligonucleotide, a nuclease or a ribozyme.

Inhibitors of βig-h3 gene expression for use in the present invention may be based on antisense oligonucleotide constructs. Anti-sense oligonucleotides, including anti-sense RNA molecules and anti-sense DNA molecules, would act to directly block the translation of βig-h3 mRNA by binding thereto and thus preventing protein translation or increasing mRNA degradation, thus decreasing the level of βig-h3, and thus activity, in a cell. For example, antisense oligonucleotides of at least about 15 bases and complementary to unique regions of the mRNA transcript sequence encoding βig-h3 can be synthesized, e.g., by conventional phosphodiester techniques and administered by e.g., intravenous injection or infusion. Methods for using antisense techniques for specifically inhibiting gene expression of genes whose sequence is known are well known in the art (e.g. see U.S. Pat. Nos. 6,566,135; 6,566,131; 6,365,354; 6,410,323; 6,107,091; 6,046,321; and 5,981,732).

Small inhibitory RNAs (siRNAs) can also function as inhibitors of βig-h3 gene expression for use in the present invention. βig-h3 gene expression can be reduced by using small double stranded RNA (dsRNA), or a vector or construct causing the production of a small double stranded RNA, such that βig-h3 gene expression is specifically inhibited (i.e. RNA interference or RNAi). Methods for selecting an appropriate dsRNA or dsRNA-encoding vector are well known in the art for genes whose sequence is known (e.g. see Tuschi, T. et al. (1999); Elbashir, S. M. et al. (2001); Hannon, G J. (2002); McManus, M T. et al. (2002); Brummelkamp, T R. et al. (2002); U.S. Pat. Nos. 6,573,099 and 6,506,559; and International Patent Publication Nos. WO 01/36646, WO 99/32619, and WO 01/68836).

Examples of said siRNAs against βig-h3 include, but are not limited to, those described in Chaoyu Ma (2008) Genes & Development 22:308-321.

Ribozymes can also function as inhibitors of βig-h3 gene expression for use in the present invention. Ribozymes are enzymatic RNA molecules capable of catalyzing the specific cleavage of RNA. The mechanism of ribozyme action involves sequence specific hybridization of the ribozyme molecule to complementary target RNA, followed by endonucleolytic cleavage. Engineered hairpin or hammerhead motif ribozyme molecules that specifically and efficiently catalyze endonucleolytic cleavage of βig-h3 mRNA sequences are thereby useful within the scope of the present invention. Specific ribozyme cleavage sites within any potential RNA target are initially identified by scanning the target molecule for ribozyme cleavage sites, which typically include the following sequences, GUA, GUU, and GUC. Once identified, short RNA sequences of between about 15 and 20 ribonucleotides corresponding to the region of the target gene containing the cleavage site can be evaluated for predicted structural features, such as secondary structure, that can render the oligonucleotide sequence unsuitable. The suitability of candidate targets can also be evaluated by testing their accessibility to hybridization with complementary oligonucleotides, using, e.g., ribonuclease protection assays.

Antisense oligonucleotides, siRNAs and ribozymes useful as inhibitors of βig-h3 gene expression can be prepared by known methods. These include techniques for chemical synthesis such as, e.g., by solid phase phosphoramadite chemical synthesis. Alternatively, anti-sense RNA molecules can be generated by in vitro or in vivo transcription of DNA sequences encoding the RNA molecule. Such DNA sequences can be incorporated into a wide variety of vectors that incorporate suitable RNA polymerase promoters such as the T7 or SP6 polymerase promoters. Various modifications to the oligonucleotides of the invention can be introduced as a means of increasing intracellular stability and half-life. Possible modifications include but are not limited to the addition of flanking sequences of ribonucleotides or deoxyribonucleotides to the 5' and/or 3' ends of the molecule, or the use of phosphorothioate or 2'-O-methyl rather than phosphodiesterase linkages within the oligonucleotide backbone.

Antisense oligonucleotides, siRNAs and ribozymes of the invention may be delivered in vivo alone or in association with a vector. In its broadest sense, a "vector" is any vehicle capable of facilitating the transfer of the antisense oligonucleotide, siRNA or ribozyme nucleic acid to the cells and preferably cells expressing βig-h3. Preferably, the vector transports the nucleic acid to cells with reduced degradation relative to the extent of degradation that would result in the absence of the vector. In general, the vectors useful in the invention include, but are not limited to, plasmids, phagemids, viruses, other vehicles derived from viral or bacterial sources that have been manipulated by the insertion or incorporation of the antisense oligonucleotide, siRNA or ribozyme nucleic acid sequences. Viral vectors are a preferred type of vector and include, but are not limited to nucleic acid sequences from the following viruses: retrovirus, such as moloney murine leukemia virus, harvey murine sarcoma virus, murine mammary tumor virus, and rouse sarcoma virus; adenovirus, adeno-associated virus; SV40-type viruses; polyoma viruses; Epstein-Barr viruses; papilloma viruses; herpes virus; vaccinia virus; polio virus; and RNA virus such as a retrovirus. One can readily employ other vectors not named but known to the art.

Preferred viral vectors are based on non-cytopathic eukaryotic viruses in which non-essential genes have been replaced with the gene of interest. Non-cytopathic viruses include retroviruses (e.g., lentivirus), the life cycle of which involves reverse transcription of genomic viral RNA into DNA with subsequent proviral integration into host cellular DNA. Retroviruses have been approved for human gene therapy trials. Most useful are those retroviruses that are replication-deficient (i.e., capable of directing synthesis of the desired proteins, but incapable of manufacturing an infectious particle). Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are provided in KRIEGLER (A Laboratory Manual," W. H. Freeman C.O., New York, 1990) and in MURRY ("Methods in Molecular Biology," vol. 7, Humana Press, Inc., Cliffton, N.J., 1991).

Preferred viruses for certain applications are the adenoviruses and adeno-associated viruses, which are double-stranded DNA viruses that have already been approved for human use in gene therapy. The adeno-associated virus can be engineered to be replication deficient and is capable of infecting a wide range of cell types and species. It further has advantages such as, heat and lipid solvent stability; high transduction frequencies in cells of diverse lineages, including hemopoietic cells; and lack of superinfection inhibition thus allowing multiple series of transductions. Reportedly, the adeno-associated virus can integrate into human cellular DNA in a site-specific manner, thereby minimizing the possibility of insertional mutagenesis and variability of inserted gene expression characteristic of retroviral infection. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

Other vectors include plasmid vectors. Plasmid vectors have been extensively described in the art and are well known to those of skill in the art. See e.g., SANBROOK et al., "Molecular Cloning: A Laboratory Manual," Second Edition, Cold Spring Harbor Laboratory Press, 1989. In the last few years, plasmid vectors have been used as DNA vaccines for delivering antigen-encoding genes to cells in vivo. They are particularly advantageous for this because they do not have the same safety concerns as with many of the viral vectors. These plasmids, however, having a promoter compatible with the host cell, can express a peptide from a gene operatively encoded within the plasmid. Some commonly used plasmids include pBR322, pUC18, pUC19, pRC/CMV, SV40, and pBlueScript. Other plasmids are well known to those of ordinary skill in the art. Additionally, plasmids may be custom designed using restriction enzymes and ligation reactions to remove and add specific fragments of DNA. Plasmids may be delivered by a variety of parenteral, mucosal and topical routes. For example, the DNA plasmid can be injected by intramuscular, intradermal, subcutaneous, or other routes. It may also be administered by intranasal sprays or drops, rectal suppository and orally. It may also be administered into the epidermis or a mucosal surface using a gene-gun. The plasmids may be given in an aqueous solution, dried onto gold particles or in association with another DNA delivery system including but not limited to liposomes, dendrimers, cochleate and microencapsulation.

Method of Preventing or Treating Pancreas Cancer

The present invention further contemplates a method of preventing or treating pancreatic ductal adenocarcinoma in a subject comprising administering to the subject a therapeutically effective amount of a βig-h3 antagonist.

In one aspect, the present invention provides a method of inhibiting pancreatic tumor growth in a subject comprising administering a therapeutically effective amount of a βig-h3 antagonist.

By a "therapeutically effective amount" of a βig-h3 antagonist as above described is meant a sufficient amount of the antagonist to prevent or treat a pancreatic ductal adenocarcinoma. It will be understood, however, that the total daily usage of the compounds and compositions of the present invention will be decided by the attending physician within the scope of sound medical judgment. The specific therapeutically effective dose level for any particular subject will depend upon a variety of factors including the disorder being treated and the severity of the disorder; activity of the specific compound employed; the specific composition employed, the age, body weight, general health, sex and diet of the subject; the time of administration, route of administration, and rate of excretion of the specific compound employed; the duration of the treatment; drugs used in combination or coincidential with the specific polypeptide employed; and like factors well known in the medical arts. For example, it is well within the skill of the art to start doses of the compound at levels lower than those required to achieve the desired therapeutic effect and to gradually increase the dosage until the desired effect is achieved. However, the daily dosage of the products may be varied over a wide range from 0.01 to 1,000 mg per adult per day. Preferably, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the subject to be treated. A medicament typically contains from about 0.01 mg to about 500 mg of the active ingredient, preferably from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

The invention also relates to a method for treating a PDAC in a subject having a high level of βig-h3 in blood with a βig-h3 antagonist.

The invention also relates to βig-h3 antagonist for use in the treatment of a PDAC in a subject having a high level of βig-h3 in blood.

The above method and use comprise the step of measuring the level of βig-h3 protein in a blood sample obtained from said subject wherein and compared to a reference control value.

A high level of βig-h3 is predictive of a high risk of having or developing a pancreatic ductal adenocarcinoma and means that βig-h3antagonist must be used.

Typically, a body fluid sample is obtained from the subject and the level of βig-h3 is measured in this sample. Indeed, statistical analyses revealed that decreasing βig-h3 levels would be particularly beneficial in those patients displaying high levels of βig-h3.

Pharmaceutical Compositions of the Invention

The βig-h3 antagonist as described above may be combined with pharmaceutically acceptable excipients, and optionally sustained-release matrices, such as biodegradable polymers, to form therapeutic compositions.

Accordingly, the present invention relates to a pharmaceutical composition comprising a βig-h3 antagonist according to the invention and a pharmaceutically acceptable carrier.

The present invention also relates to a pharmaceutical composition for use in the prevention or treatment of pancreatic ductal adenocarcinoma comprising a βig-h3 antagonist according to the invention and a pharmaceutically acceptable carrier.

"Pharmaceutically" or "pharmaceutically acceptable" refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

In therapeutic applications, compositions are administered to a patient already suffering from a disease, as described, in an amount sufficient to cure or at least partially stop the symptoms of the disease and its complications. An appropriate dosage of the pharmaceutical composition is readily determined according to any one of several well-established protocols. For example, animal studies (for example on mice or rats) are commonly used to determine the maximal tolerable dose of the bioactive agent per kilogram of weight. In general, at least one of the animal species tested is mammalian. The results from the animal studies can be extrapolated to determine doses for use in other species, such as humans for example. What constitutes an effective dose also depends on the nature and severity of the disease or condition, and on the general state of the patient's health.

In therapeutic treatments, the antagonist contained in the pharmaceutical composition can be administered in several dosages or as a single dose until a desired response has been achieved. The treatment is typically monitored and repeated dosages can be administered as necessary. Compounds of the invention may be administered according to dosage regimens established whenever inactivation of βig-h3 is required.

The daily dosage of the products may be varied over a wide range from 0.01 to 1,000 mg per adult per day. Preferably, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the patient to be treated. A medicament typically contains from about 0.01 mg to about 500 mg of the active ingredient, preferably from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 10 mg/kg of body weight per day. It will be understood, however, that the specific dose level and frequency of dosage for any particular patient may be varied and will depend upon a variety of factors including the activity of the specific compound employed, the metabolic stability, and length of action of that compound, the age, the body weight, general health, sex, diet, mode and time of administration, rate of excretion, drug combination, the severity of the particular condition, and the host undergoing therapy.

In the pharmaceutical compositions of the present invention for oral, sublingual, subcutaneous, intramuscular, intravenous, transdermal, local or rectal administration, the active principle, alone or in combination with another active principle, can be administered in a unit administration form, as a mixture with conventional pharmaceutical supports, to animals and human beings. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms.

The appropriate unit forms of administration include forms for oral administration, such as tablets, gelatine capsules, powders, granules and solutions or suspensions to be taken orally, forms for sublingual and buccal administration, aerosols, implants, forms for subcutaneous, intramuscular, intravenous, intranasal or intraocular administration and forms for rectal administration.

In the pharmaceutical compositions of the present invention, the active principle is generally formulated as dosage units containing from 0.5 to 1000 mg, preferably from 1 to 500 mg, more preferably from 2 to 200 mg of said active principle per dosage unit for daily administrations.

When preparing a solid composition in the form of tablets, a wetting agent such as sodium laurylsulfate can be added to the active principle optionally micronized, which is then mixed with a pharmaceutical vehicle such as silica, gelatine, starch, lactose, magnesium stearate, talc, gum arabic or the like. The tablets can be coated with sucrose, with various polymers or other appropriate substances or else they can be treated so as to have a prolonged or delayed activity and so as to release a predetermined amount of active principle continuously.

A preparation in the form of gelatin capsules is obtained by mixing the active principle with a diluent such as a glycol or a glycerol ester and pouring the mixture obtained into soft or hard gelatine capsules.

A preparation in the form of a syrup or elixir can contain the active principle together with a sweetener, which is preferably calorie-free, methyl-paraben and propylparaben as an antiseptic, a flavoring and an appropriate color.

The water-dispersible powders or granules can contain the active principle mixed with dispersants or wetting agents, or suspending agents such as polyvinyl-pyrrolidone, and also with sweeteners or taste correctors.

Rectal administration is effected using suppositories prepared with binders which melt at the rectal temperature, for example cacao butter or polyethylene glycols.

Parenteral, intranasal or intraocular administration is effected using aqueous suspensions, isotonic saline solutions or sterile and injectable solutions which contain pharmacologically compatible dispersants and/or wetting agents, for example propylene glycol, butylene glycol, or polyethylene glycol.

Thus a cosolvent, for example an alcohol such as ethanol or a glycol such as polyethylene glycol or propylene glycol, and a hydrophilic surfactant such as TWEEN® (Polysorbate), can be used to prepare an aqueous solution injectable by intravenous route. The active principle can be solubilized by a triglyceride or a glycerol ester to prepare an oily solution injectable by intramuscular route.

Transdermal administration is effected using multilaminated patches or reservoirs into which the active principle is in the form of an alcoholic solution.

Administration by inhalation is effected using an aerosol containing for example sorbitan trioleate or oleic acid together with trichlorofluoromethane, dichlorotetrafluoroethane or any other biologically compatible propellant gas.

The active principle can also be formulated as microcapsules or microspheres, optionally with one or more carriers or additives.

Among the prolonged-release forms which are useful in the case of chronic treatments, implants can be used. These can be prepared in the form of an oily suspension or in the form of a suspension of microspheres in an isotonic medium.

The active principle can also be presented in the form of a complex with a cyclodextrin, for example .alpha.-, .beta.- or .gamma.-cyclodextrin, 2-hydroxypropyl-.beta.-cyclodextrin or methyl-.beta.-cyclodextrin.

FIGURES

FIG. 1. The main source of βig-h3 in neoplasic lesions is the CAFs.

A. Protocol isolation of ductal cells and CAFs. B. Relative expression of βig-h3 in ductal and CAF isolated compartments (RT-qPCR using TBP as a house keeping reference gene). C βig-h3 production by CAF in control ex vivo condition of stimulated for 24 h with TGF-β1. **$P<0.01$ FIG. 2. Soluble βig-h3 production in the microenvironment of the tumor is able to modulate specific $CD8^+$ T cell responses.

βig-h3 directly modulates $CD8^+$ T cell activation. OT1 T cells were pretreated with rβig-h3 for 24 h and then Ag-specific activated by adding OVA peptide at 2 different concentrations (10 and 1 ng/ml). Pretreated conditions are represented in red. Not treated conditions are represented in gray. A) Quantification of the divided $CFSE^{low}$ OT1 cell after 98 h of in vitro cell culture B) Quantification of the total number of OT1 cells after 98 h of in vitro cell culture, B) Quantification of the activated $CD69^+OT1$ cells after 98 h of in vitro cell culture C) Quantification of the activated $CD44^+$ OT1 cells after 98 h of in vitro cell culture. D) Quantification of the total number of $CD69^+OT1$ cells after 98 h of in vitro cell culture, E) Quantification of the number of OT1 in presence/absence of CAF cells and anti-βig-h3 neutralizing Ab or control Ab cells after 98 h of in vitro cell culture F) Quantification of the number of OT1 cells in presence/absence of CAF supernatant and with anti-βig-h3 neutralizing Ab or control Ab cells after 98 h of in vitro cell culture. G) Quantification of anti-tumoral $CD8^+$ T cells from draining lymph nodes (DLN) of p48;Kras mice after 5 days in culture with tumoral cell line (KC). Representative of 3 independent experiments. *$P<0.05$. **$P<0.01$ FIG. 3. βig-h3 depletion enhances T cell responses in vivo.

Quantification of intra-pancreatic $CD8^+$ T cells (A), EPCAM (ductal tumoral compartment) (B) and αSMA(CAF compartment) (C). Representative of 3 independent experiments *$P<0.05$. **$P<0.01$ FIG. 4. βig-h3 can be used as a marker of early neoplasic development A. ELISA determination of the amount of βig-h3 in WT and KC mice at the age of 2 months. B) ELISA determination of the amount of βig-h3 in the sera of 20 healthy volunteers and 20 PDAC patients. *$P<0.05$, ***$<0.001$.

FIG. 5. βig-h3 signals through CD61 on the surface of T cells. (A) Mean fluorescence intensity (MFI) of CD61 expression on $CD8^+$ T cells in spleen and in tumor. (B) MFI of CD61 expression in $CD8^+$ T cells βig-h3-treated or not treated (0) for 24 h. (C) Confocal colocalisation of CD61 with pLck Y505 was calculated using Zen sofware according to Manders method. At least 20 images were analyzed for each molecule. The results are representative of 3 independent experiments. ****$P<0.0001$.

FIG. 6. CD8+ T cells are instrumental for the βig-h3 neutralization effect on tumor growth. (A) Experimental setting. FACS analysis of the percentage of CD45 (B), percentage of CD8+ T cells among CD45+ cells (C) percentage of EPCAM– among CD45-cells (D). (E) Experimental setting. (F) FACS analysis of the percentage of EPCAM– among CD45-cells. The results are representative of 2 independent experiments. *$P<0.05$.

FIG. 7 Additional cohort of sera of 49 healthy volunteers from blood bank and 104 patients with PDAC for the presence of soluble βig-h3 as a potential diagnosis marker. ELISA determination of the amount of βig-h3 in the sera ***$P<0.001$.

EXAMPLE 1

Material & Methods

Mouse Models p48-Cre;Kras$^{G12D}$ were bred and housed in specific pathogen-free conditions and used as a model of development of PANINs. These mice develop PANIN lesions starting from 1.5 months. In order to determine the role of βig-h3 molecule in the regulation of specific immune response OT1/Rag2 KO transgenic mice expressing unique OT1 T cell receptor ($CD8^+$ T cells) were used. Furthermore, a neutralizing antibody against βigh3 was used in order to assess the impact of the molecule in the early stages of PANIN development.

Mouse pancreas of p48-Cre;Kras$^{G12D}$ or WT animals were isolated by collagen disruption. Ducts were isolated using DBA-lectin—FITC and subsequent anti-FITC magnetic beads and CAFs by using anti-PDGFRα-PE and anti-PE magnetic beads and MACS Miltenyi technology. Alternatively, for increase purity we FACS sort them. The purified populations were injected in Matrigel in recipient mice (immunocompetant WT C57B16 mice). Antibody i.p injection with anti-TGFBIp neutralizing monoclonal antibody (provided by In-San Kim, Korea Institute of Science and Technology Seoul, Korea) or control monoclonal antibody (BioXCell, USA) at a concentration of 300 µg/kg was done in p48-Cre;Kras$^{G12D}$ once per week for 4 weeks. Altenatively, p48-Cre;Kras$^{G12D}$ cell line (2 different cell lines generated as described previously by Agbunag et al., 2006 from pancreata of p48-Cre;Kras$^{G12D}$ 2.5 month old mice), infused with anti-TGFBIp neutralizing monoclonal antibody or control Ab were sc injected in matrigel in immunocompetent WT C57B16 mice.

The impact of T cell population on the tumor tumorigenesis after s.c. transplantation can be assessed by antibody depletion with anti-CD8 (CD8$^+$ T cells), anti-CD4 (CD4$^+$ T cells) or anti-Gr1 (for monocytes/macrophages) all from BioXCell, USA.

Biological Resources

Pancreas slides from patients with PANINs, IPMN or PDAC were collected from Bucarest, Romanian National Institute for Diabetes, Marseille Hopital La Timone and Lyon, Hopital Edouard Herriot. 6-μm sections from paraffin embedded pancreas were stained for immunhistochemistry and immuno fluoresce. All experimental procedures were approved by Romanian National Ethics Committee and French National Ethics Committee. Sera were recovered from CRB (Centre de Ressources Biologiques Centre Leon Berard, Lyon France) BB-0033-00050.

Cell Culture

Cells extracted from draining lymph nodes, pancreas (by collagenase distruption as previously described Agbunag et al., 2006), spleen were cultured in 96-U-shaped-well plates (300 000 cells/well) in presence of neutralizing anti-βigh3 Ab or control Ab (BioXCell, USA) at a final concentration of 6 μg/ml for 24 hours.

Flow Cytometry Analysis

For extracellular staining, draining lymph nodes cells or perfused pancreata were stained with CD8 V450 rat antibody (BD Bioscience), mouse CD4 V500 rat antibody (BD Bioscience), mouse CD44 A700 rat antibody (BD Bioscience), CD69 FITC (ImmunoTools). For intracellular staining, draining lymph nodes cells were activated with PMA and ionomycin (1 μg/ml) for 4 hrs at 37° C. in 5% $CO_2$ in RPMI 1640 medium (Invitrogen) supplemented with 10% FCS (Biowest), 10 mM HEPES, 100 U/ml penicillin G, 100 μg/ml streptomycin, 2 mM L-glutamine (Invitrogen) in the presence of Golgi plug (BD Pharmingen). After activation, cells were stained with CD8 V450 rat antibody (BD Bioscience), mouse CD4 V500 rat antibody (BD Bioscience), permeabilized using Cytofix-Cytoperm (BD Pharmingen) and further stained with anti-IFNγ (clone XMG1.2, BD Pharmingen), anti-Granzyme B (clone GB12, Invitrogen) and. Flow cytometry analyses was carried out with BD Fortessa Flow Cytometer (BD Biosciences) and analyzed with either BD FACS Diva software v5.0.1 (BD) or FlowJo (Tree Star, Inc.).

Reverse Transcription and qPCR

RNAs were extracted by Qiagen kit from pelleted islets according to the manufacturer. RNA concentrations were measured at Nanodrop. Reverse transcription (RT) was made on equivalent quantity of extracted RNAs (superior to 300 ng). From cDNA, quantitative Polymerase Chain Reaction (qPCR) was made with Power SYBR® Master Mix (Life technologies) with following primers, TBP Forward 5'-TGGTGTGCACAGGAGCCAAG-3'(SEQ ID N° 3), TBP Reverse 5'-TTCACATCACAGCTCCCCAC-3'(SEQ ID N° 4) and βig-h3 All-in-one™ qPCR (cat no MQP028379) primers from GeneCopoeia.

Immunofluorescence and Confocal Microscopy

Slides with 5 μm sections of mouse pancreas included in paraffin were deparaffined. Sections were unmasked by unmasking solution (Vector H 3300) then saturated with antibody diluent (Dako) during 30 minutes and incubated with primary antibody diluted in antibody diluent over night at 4° C. (βig-h3 rabbit antibody from Sigma, αSMA from Genetex, CK19 CK19 Troma III from DSHB). For cultured cells, cells were cytospined on slides and fixed in 0.4% paraformaldehyde for 10 min and then permeabilized in 0.1% TRITONX-100® (octyl phenol ethoxylate) for 10 min. Cells were washed in PBS 0.05% TWEEN® (polysorbate) and the blocked with antibody diluent (Dako) 15 min before staining o.n. at 4° C. with, βig-h3 rabbit antibody from Sigma, CD61 from Ebioscience, pErk from Cell Signalling. Slides were incubated with species specific anti-Fab'2-Alexa 647 and Alexa 555 (Molecular Probes) and mount with Vectashield Mounting medium with DAPI. Representative images of the localization of each molecule are shown. All confocal analysis were multiple repeats, and at least 20 images were analyzed for each molecule. The method use for colocalization quantifications was previously described (10). Data were rendered and analyzed using Zen software (Zeiss).

Statistical Analysis

P values were calculated with Student's t test, (GraphPad Prism) as specified in figure legends. *P<0.05; P<0.01; *P<0.001. ****P<0.0001

Results

βig-h3 is Expressed Early in Tumorigenesis in Pancreatic Neoplasia

We have previously shown that in WT pancreas in C57B16βig-h3 protein is expressed at low levels in islets of Langerhans (Patry et al., 2015). No expression of the protein was detected in the exocrine compartment. In contrast, in p48Cre;Kras$^{G12D}$ (KC) mice developing neoplasia starting from 1.5 months (Hingorani et al., 2003), we found a significant expression of the protein around the neoplastic lesions. This expression was maintained, but heterogeneous, at later stages of the neoplastic development (ie 4.5 and 7 months). Furthermore, we have identified by immunofluorescence staining that βig-h3 expression was localized around neoplastic ductal cells (PANINs) expressing ductal marker cytokeratin 19 (CK19) and that is was mostly colocalized with the stromal marker αSMA as soon as 1.5 months of PANIN development. In order to check for the relevance of the expression protein pattern in patients with pancreatic cancer, we have performed immunohistochemistry staining on pancreas adenocarcinoma (PDAC). 15 patients with PDAC have been analyzed and all of them showed the protein expressed in the extracellular compartment in the stroma around neoplastic ducts but also in the diffuse carcinoma. Altogether, these results demonstrate for the first time that βig-h3, a TGF-β/Activins superfamily target, is expressed early during neoplasia in mice and that this expression was found with the same pattern of staining in human PDAC.

βig-h3 is Restricted to the Microenvironment Compartment in Pancreatic Neoplasia Since the pattern of βig-h3 expression showed colocalization with αSMA, we next investigated which types of cells were producing the protein. Therefore we have isolated from 2.5 months pancreas, the ductal cells and the cancer associated fibroblasts (CAFs) by magnetic beads sorting (FIG. 1A) (described in mat&methods). After mRNA extraction we have performed qRT-PCR for βig-h3 transcript. We found that the expression of βig-h3 protein was restricted to the CAF compartment (FIG. 1B). We have confirmed these data at the level of protein since three different CAF cell lines (isolated from KC mice) were cultivated in vitro for 24 h in complete media or stimulated with TGF-β1 (20 ng/ml). We found that CAFs produce βig-h3 protein ex vivo and that this production was further potentiated by TGF-β treatment (FIG. 1C).

Secreted Sig-h3 Dampens CD8$^+$ T Cell Ag-Specific Responses

Figure 2C:
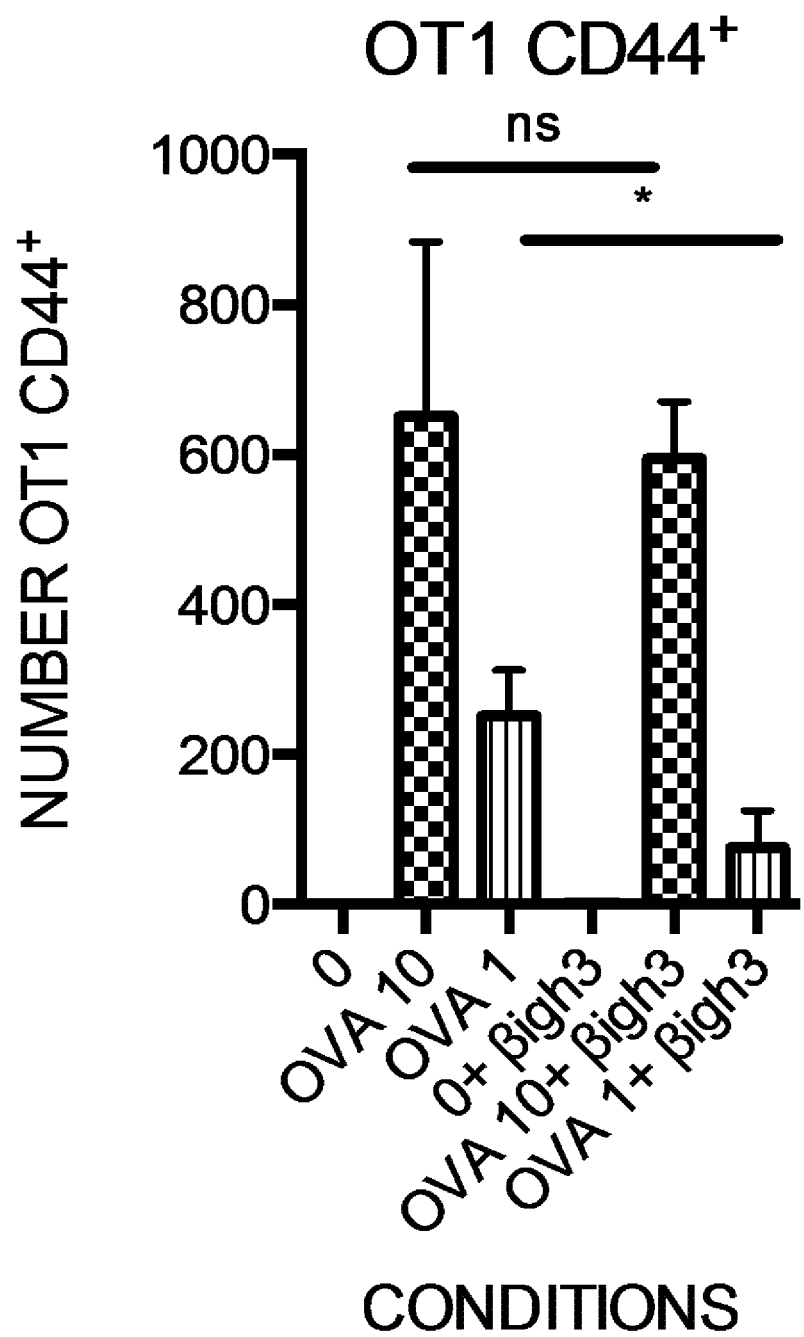
Figure 2D:
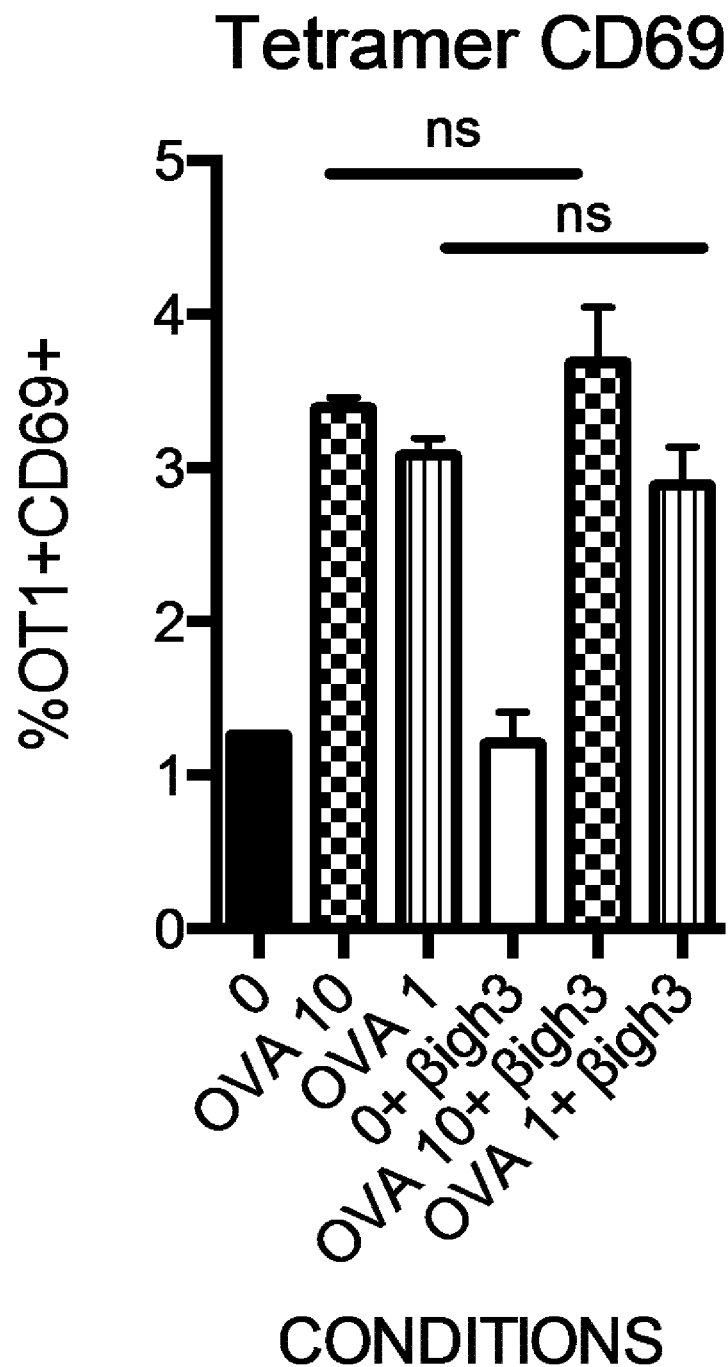
Figure 2E:
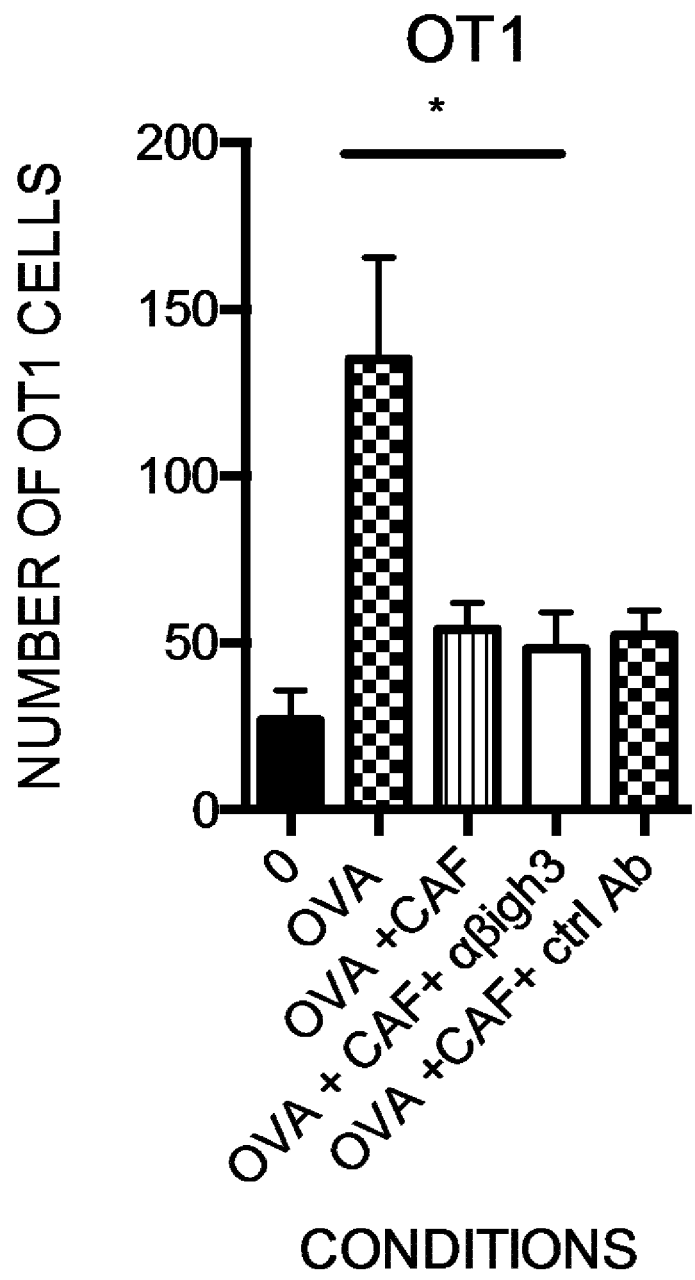
Figure 2F:
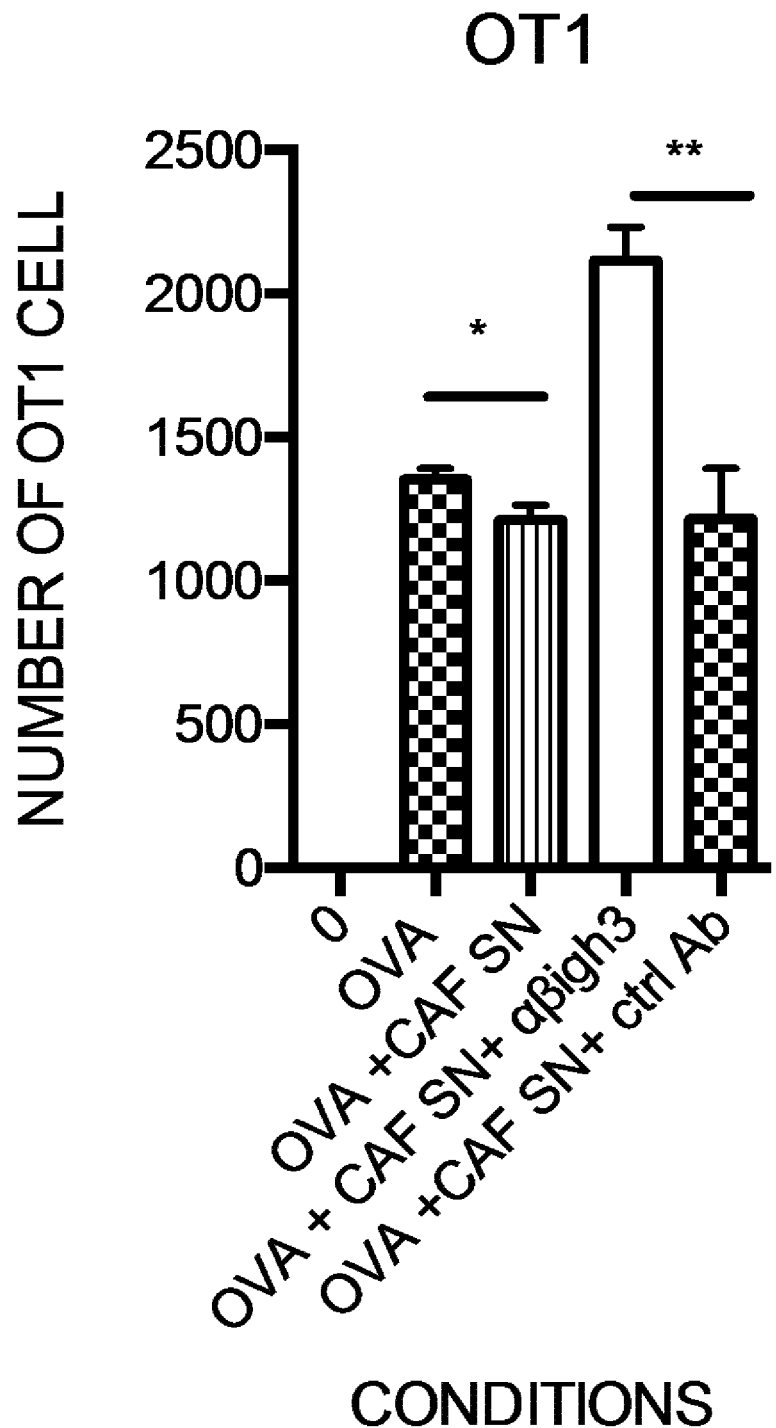
Figure 2G:
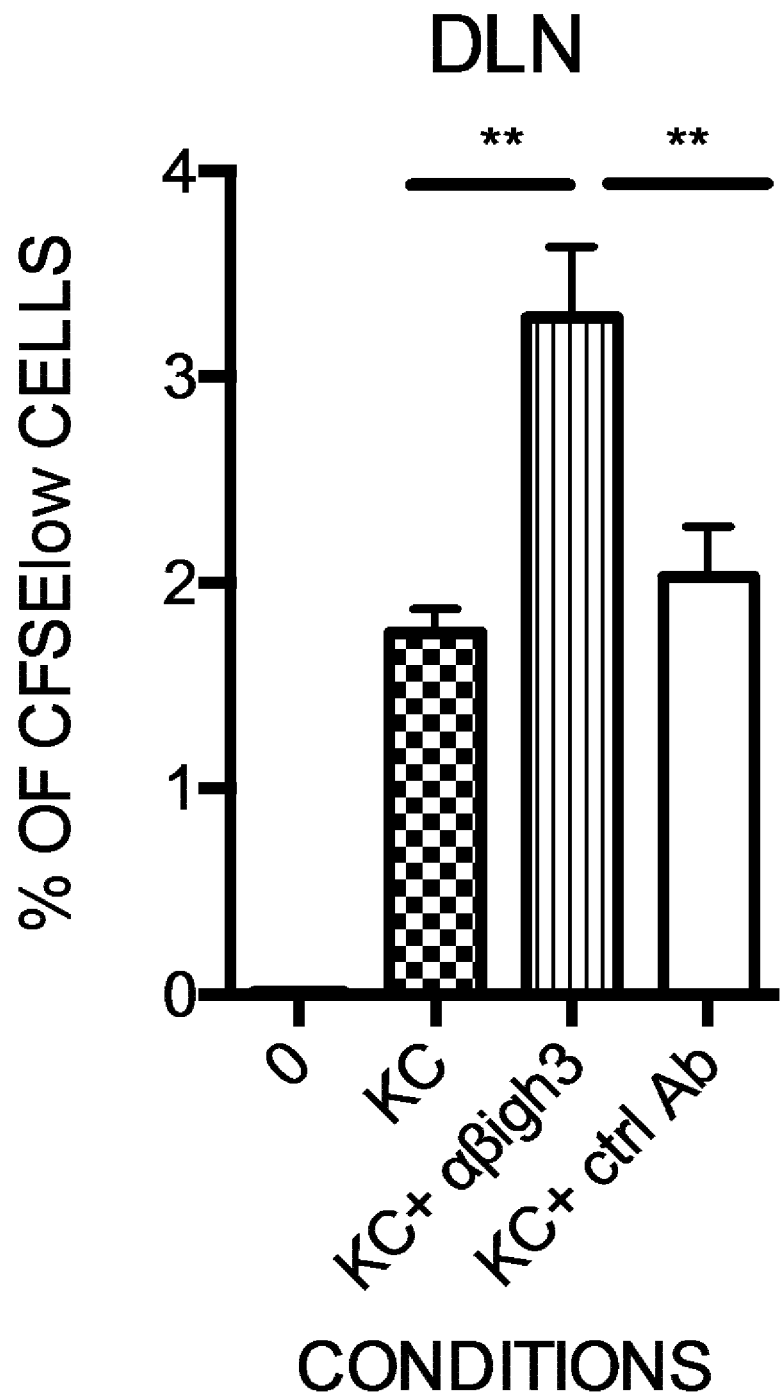

We have previously shown that βig-h3 was able to inhibit diabetogenic T cells to kill islet beta cells by directly blocking Lck kinase in inactive conformation (Patry et al., 2015). In order to determine if βig-h3 was able to modulate CD8$^+$ T cell Ag-specific responses. We treatead OT1 CD8+ T cell with recombinant βig-h3 and further treat the cells with specific OVA SIINFEKL cognate peptide (at 2 different concentrations). We demonstrate that βig-h3 pretreatment was able to significantly decrease Ag-specific responses as measured by the number of total (FIG. 2B) and dividing OT1 (FIG. 2A) cells expressing activation marker CD69 (FIG. 2D) and CD44 (FIG. 2C). We have further used a neutralizing Ab against βig-h3 in co-culture experiments of CD8$^+$ T cells with CAFs. As shown in FIG. 2E, adding of the neutralizing Ab was not able to abolish the immune-suppressive of CAFs but was able to block the secreted protein in the CAF supernatant (FIG. 2F). Furthermore, we have confirmed these results by using T cells from draining lymph of KC mice stimulated with irradiated pancreas KC cell line (FIG. 2G). Altogether, these results show for the first time that βig-h3 was able to modulate specific anti-tumoral CD8$^+$ T cell responses in vitro.

βig-h3 Neutralization In Vivo Enhances Local CD8$^+$ T Cell Response

Figure 3A:
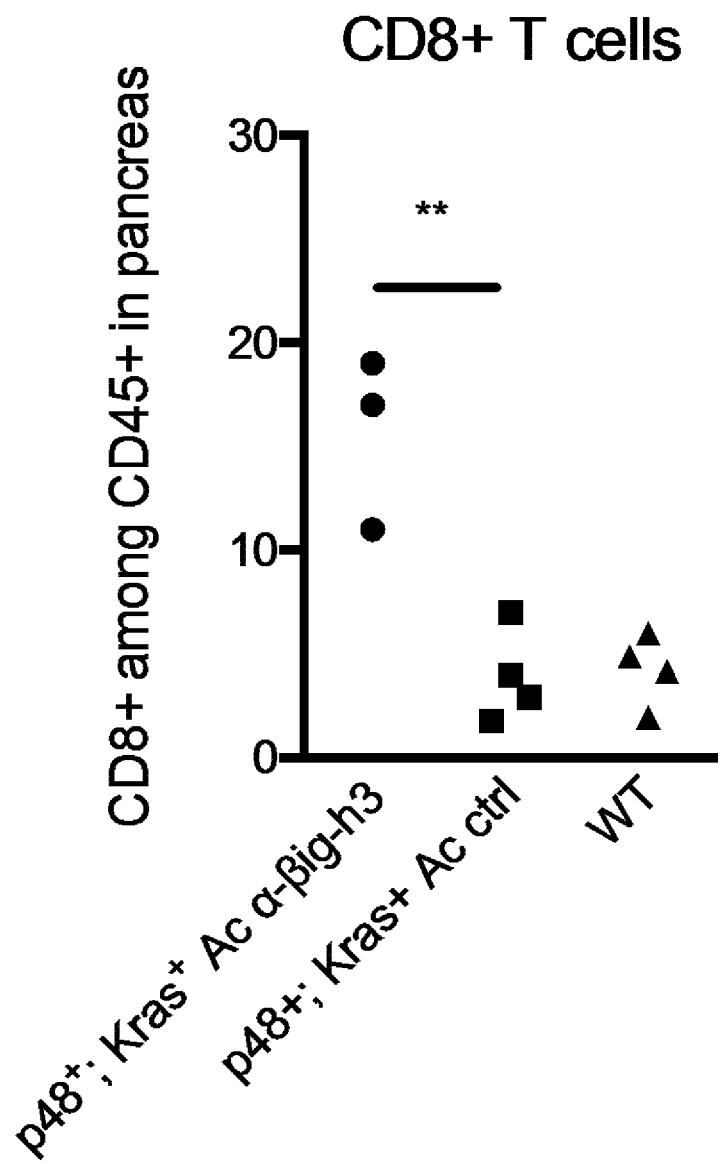
Figure 3B:
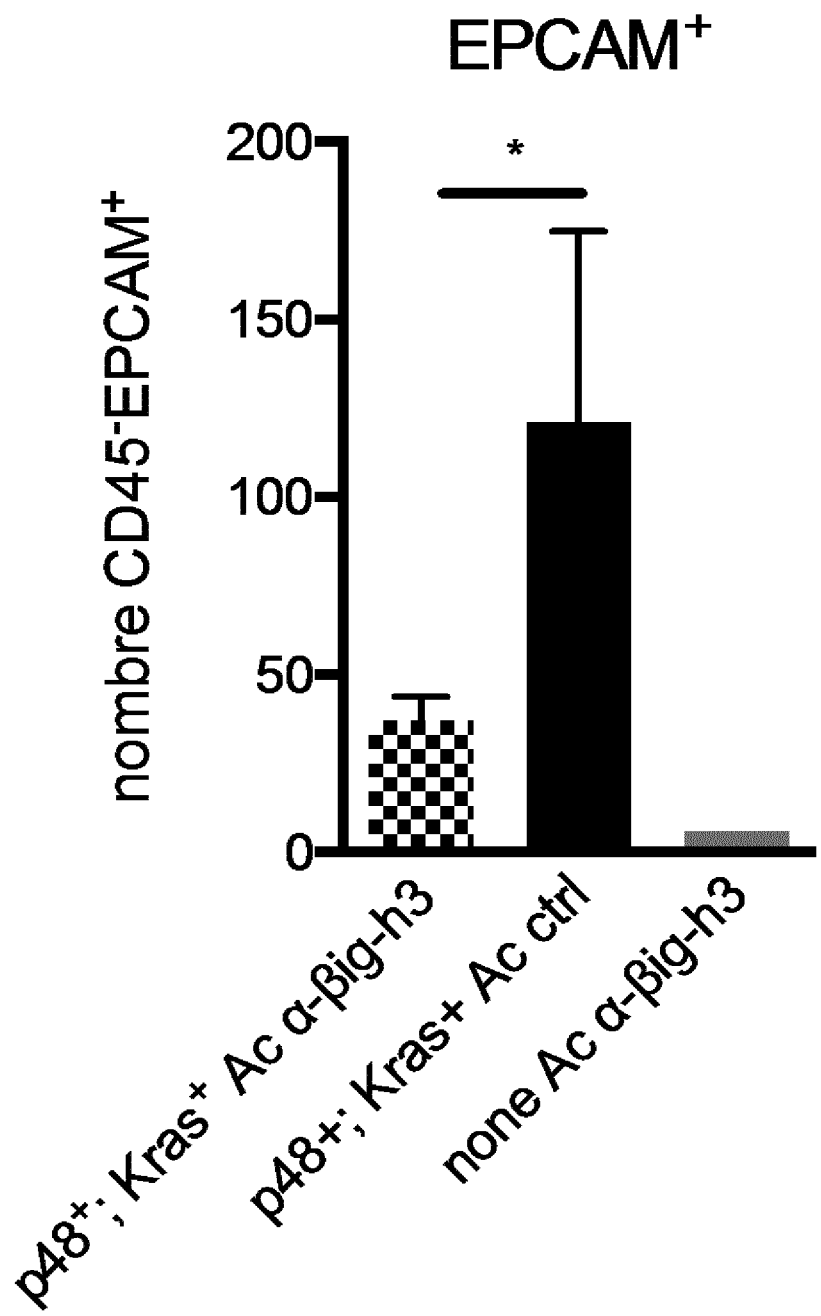
Figure 3C:
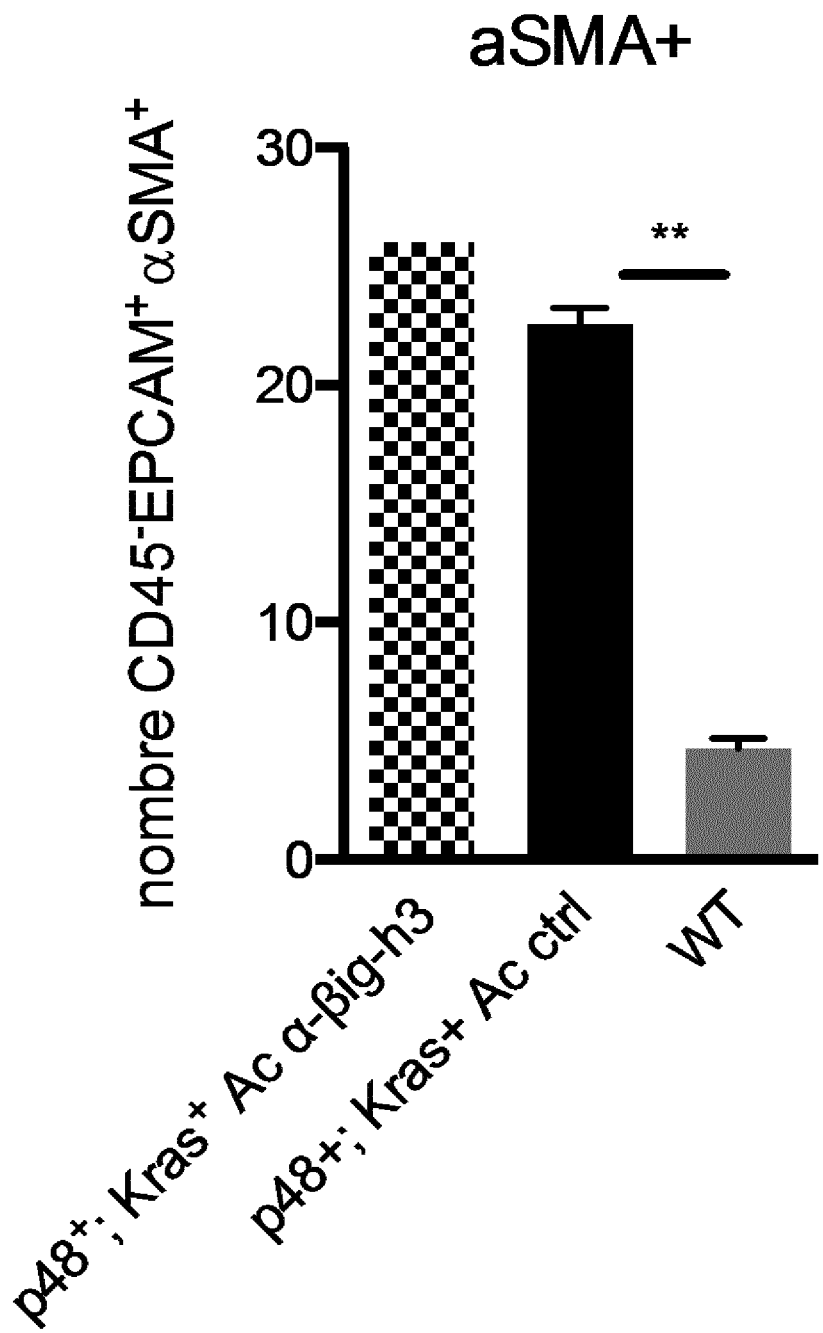

In order to test the impact in vivo we have treated KC mice with a neutralizing βig-h3 Ab or isotype control antibody starting starting from the age of 21 days (immediately after weaning). We treated the mice for once per week for 4 weeks and then evaluated the neoplasia in the pancreas by FACS staining, immunohistochemistry and immunofluorescence. Treated mice displayed reduced CK19 staining compared to littermate control Ab treated mice. Furthermore, this response was associated with increased number of CD8$^+$ T cells in neoplastic pancreas as detected by immunofluorescence and FACS analysis (FIG. 3A). We confirmed by FACS that the ductal neoplastic compartment expressing EPCAM was reduced (FIG. 3B). The number of CAFs as detected by αSMA staining was not reduced, suggesting that βig-h3 neutralization enhances CD8$^+$ anti-tumoral responses that kill the neoplastic cell without reducing the number of CAFs (only by modifying their function).

In order to test if only the local pancreatic anti-tumoral was sufficient to drive the elimination of neoplastic cells, we have performed injection of KC cell line into immunocompetent B6 mice. KC cell line treated with anti-bigh3 neutralizing Ab or control Ab were injected sc in B6 (in Matrigel) and sacrificed 10 days later. The use of βig-h3 neutralizing Ab leads to significant decrease in tumor size and weight. More importantly this results were correlated with decreased EPCAM staining and as well as CAF number (FIG. 3A, 3B) as detected by FACS staining. Furthermore, the tumor itself displayed less cancer initiating cells (as defined in the literature as CD45$^-$CD44$^+$CD24$^{low}$. Altogether these results show for the first time that βig-h3 neutralization leads to tumor elimination by enhancing the CD8 anti-tumoral response in vivo.

βig-h3 Can be Used as a Marker of Early Neoplasic Development

Figure 4A:
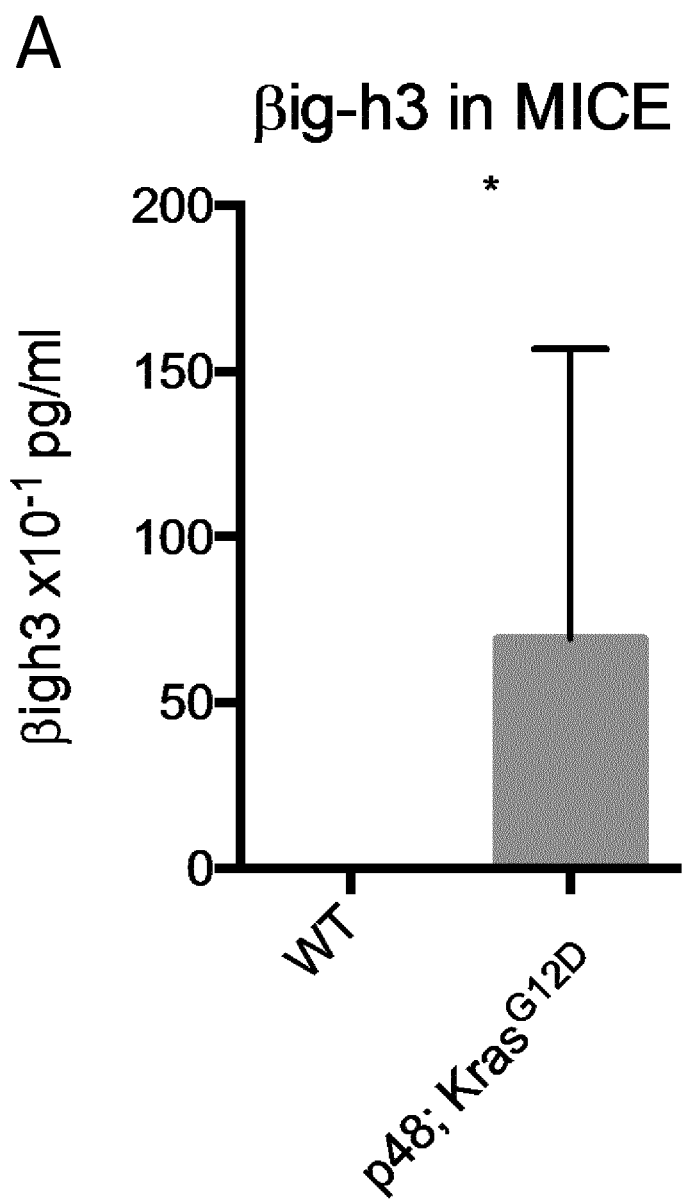

Since βig-h3 expression occurs early in pancreatic neoplasia we hypothesized that βig-h3 could be detected in the sera and use as a "predictive marker". We have use ELISA to detect the amount of βig-h3 in the sera of WT of KC mice. We have detected significant increase in the amount of bigh3 in the sera of KC mice (69.32±35.70N=6) compared to WT mice the detection was below the threshold of the ELISA test (FIG. 4A).

Figure 4B:
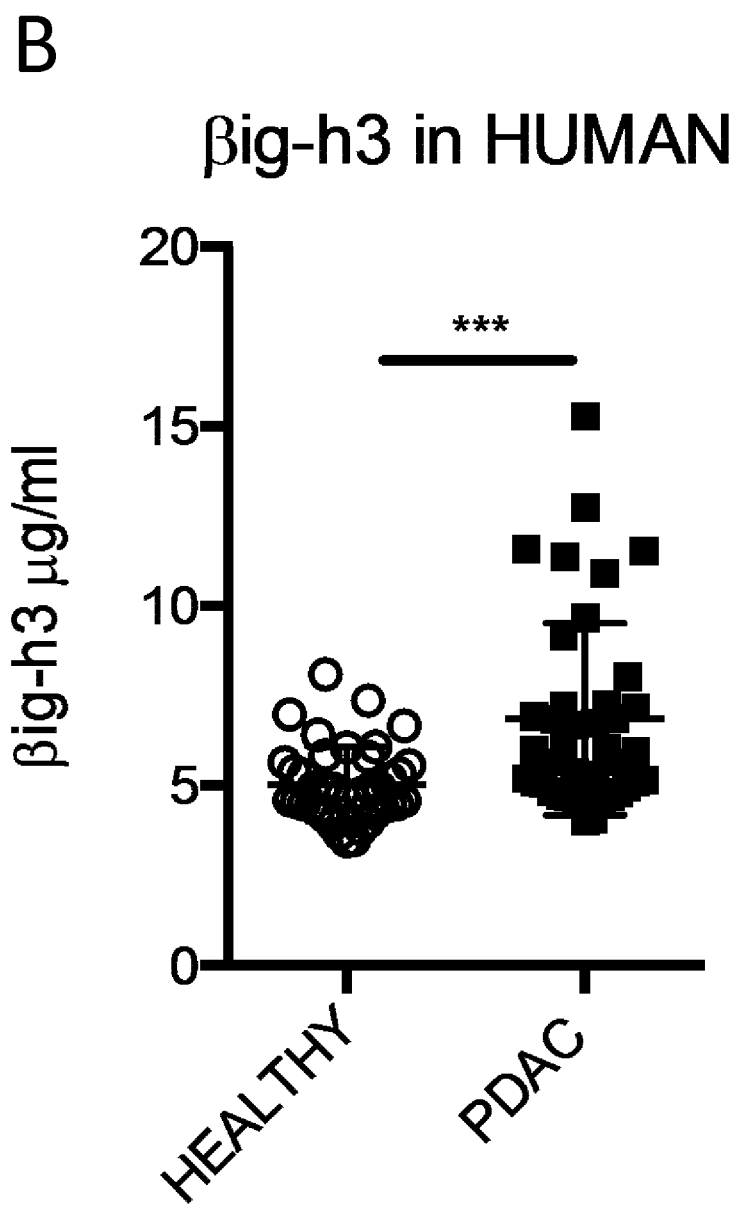

As a proof of concept in human PDAC we have tested the sera of 20 healthy volunteers from blood bank and 20 patients with PDAC for the presence of soluble βig-h3 as a potential diagnosis marker. As shown in FIG. 4B there is a significant difference between healthy volunteers and PDAC patients indicated that this molecule have potential interest as a biomarker.

Figure 5A:
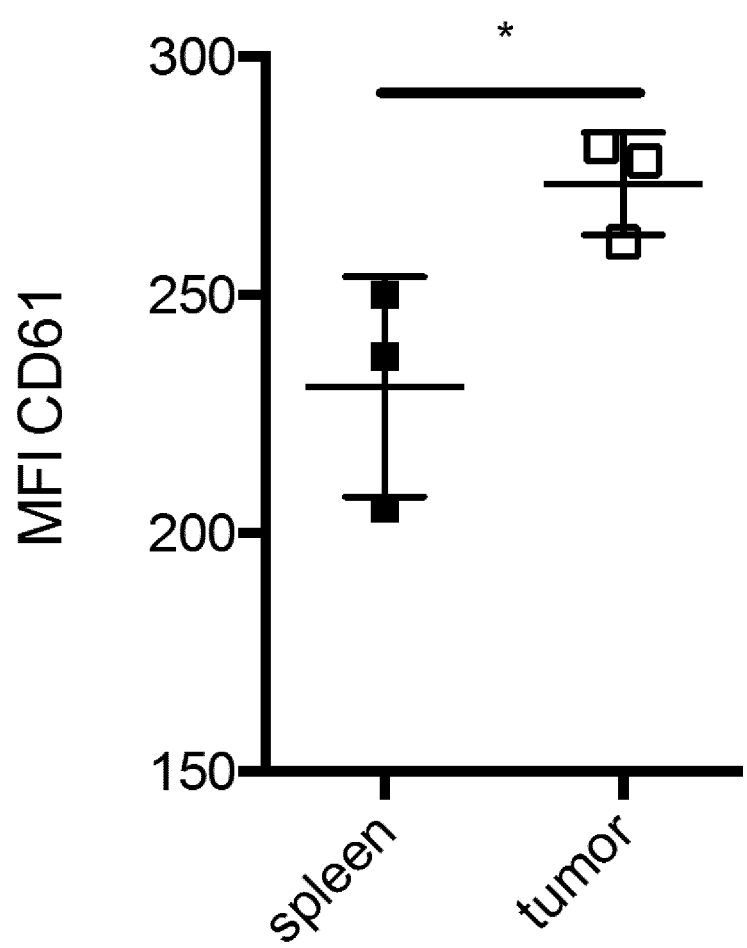
Figure 5B:
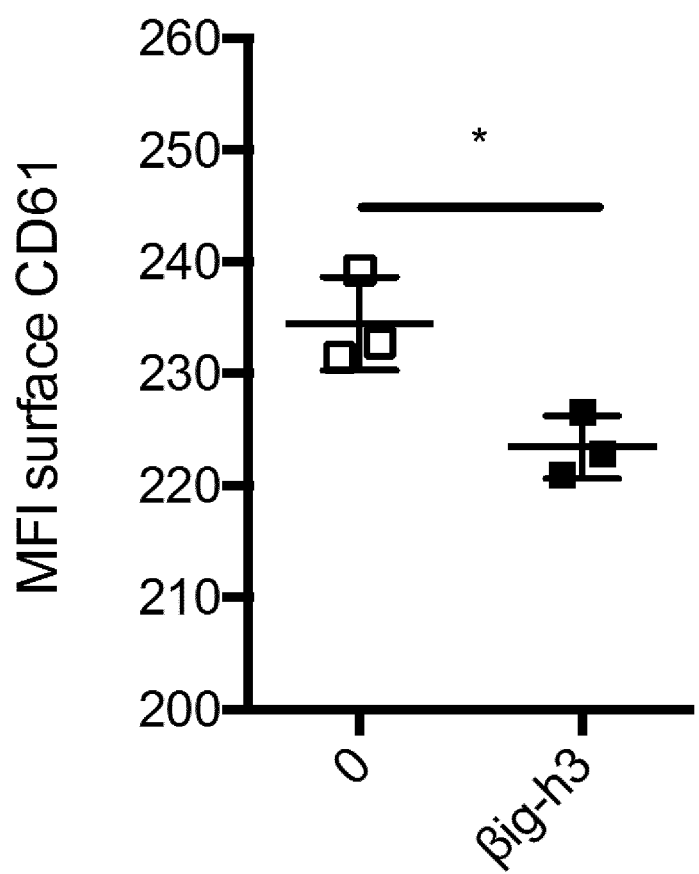
Figure 5C:
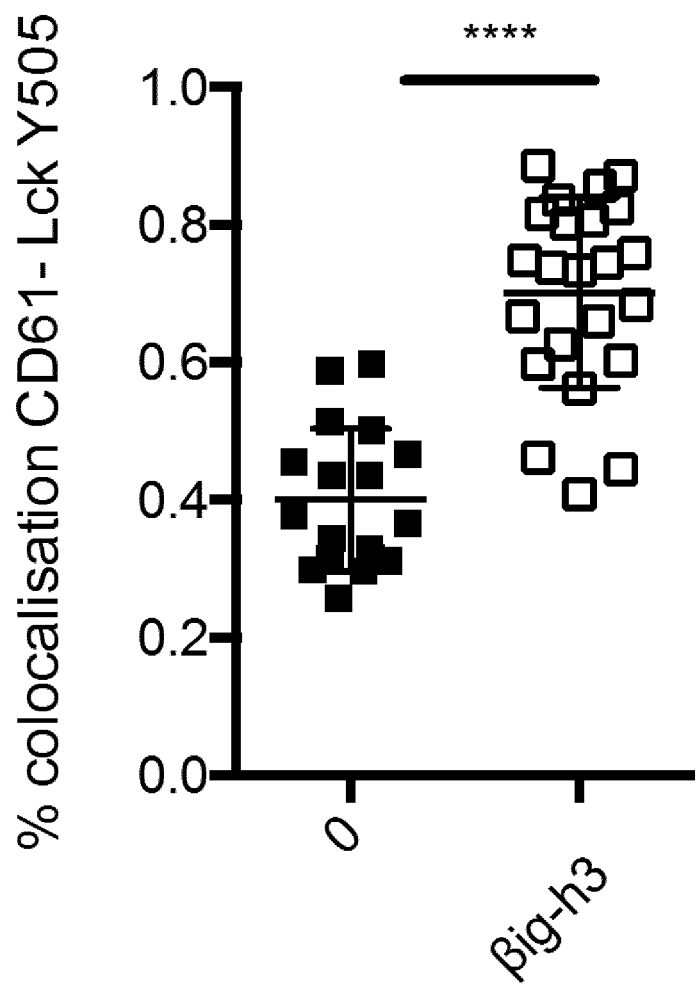

EXAMPLE 2

βig-h3 Interacts with CD61 on T Cell Surface

βig-h3 has been reported to signal through binding to αvβ3 integrins (Tumbarello D A, et al. Mol Cancer 2012; 11:36). Therefore, we searched for the expression of β3 (CD61) at the surface of CD8+ T cells. We found that both CD8+ T cell present in lymph nodes and in tumors express CD61 and further noticed that the expression of CD61 was significantly higher in tumor CD8+ T cells compared to peripheral CD8+ T cells (FIG. 5A). We next confirmed that βig-h3 was able to signal through CD61 since treatment of CD8+ T cells with recombinant βig-h3 protein (rβig-h3) led to CD61 internalization (FIG. 5B). As reported before in diabetis (Patry M, Diabetes 2015; 64:4212-9), treatment of CD8+ T cells with rβig-h3 resulted in the phosphorylation of Lck on Y505 and its colocalization with CD61 (FIG. 5C). These results show that βig-h3 interacts with CD61 at the surface of CD8+ T cells leading to the phosphorylation of Lck on Y505 (Davis S. J. Trends Immunol 2011; 32:1-5) and subsequently the blocking of this early kinase of the TCR signaling pathway.

CD8+ T Cells are Mandatory for βig-h3 Neutralization Effect In Vivo

Since βig-h3 neutralization leads to local accumulation of CD8+ T cells, we thought to investigate the direct contribution of CD8+ T cells to the process. To test this hypothesis, we injected KC cell line treated with βig-h3 neutralizing or control Ab in Rag2KO mice. The mice were further injected i.v with CD8+ T cells isolated from pancreatic-draining lymph nodes of KC mice (FIG. 6A). We found that while the mice injected with KC cell line treated with βig-h3 neutralizing Ab displayed a similar recruitment of CD45+ cells, they were showing an increased accumulation of CD8+ T cells compared to control-condition treated animals (FIGS. 6B and 6C). Moreover, concomitant to the CD8 T cell enhanced number, we detected a reduced proportion of neoplastic ductal CD45-/EPCAM+ cells (FIG. 6D). These results suggest that in absence of βig-h3, the accumulation of CD8+ T cells might be responsible for the diminished proportion of EPCAM+ cells. A prediction would be that the observed reduction of EPCAM+ population in the tumor would be rescued by CD8+ T cell depletion. To test this hypothesis, we performed sub-cutaneous implantation of KC derived cell line treated with βig-h3 neutralizing or control Ab and subsequently depleted for CD8+ T cells by 2 consecutive iv injections at day 7 and 8 post tumor-cell-injection (FIG. 6E). These treatments resulted in a depletion of more than 90% of the CD8+ T cell population without altering the CD4+ T cell or the F4/80 populations. In contrast, the neutralization of CD8 cells was sufficient to permit the establishment of the same number of EPCAM+ cell in both βig-h3 neutralized or control conditions (FIG. 6F). Altogether, these results indicate that CD8+ T cells are mandatory for the βig-h3 neutralizing effect on tumor growth in vivo.

βig-h3 Can be Used as a Marker of PDAC

As a proof of concept in human PDAC we have tested an additional cohort of sera of 49 healthy volunteers from blood bank and 104 patients with PDAC for the presence of soluble βig-h3 as a potential diagnosis marker. As shown in FIG. 7 there is a significant difference between healthy volunteers and PDAC patients indicated that this molecule have potential interest as a biomarker.

TABLE 1

Useful nucleotide and amino acid sequences for practicing the invention

| SEQ ID NO | Nucleotide or amino acid sequence |
|---|---|
| 1 (βig-h3 AA sequence) | MALFVRLLAL ALALALGPAA TLAGPAKSPY QLVLQHSRLR GRQHGPNVCA VQKVIGTNRK YFTNCKQWYQ RKICGKSTVI SYECCPGYEK VPGEKGCPAA LPLSNLYETL GVVGSTTTQL YTDRTEKLRP EMEGPGSFTI FAPSNEAWAS LPAEVLDSLV SNVNIELLNA LRYHMVGRRV LTDELKHGMT LTSMYQNSNI QIHHYPNGIV TVNCARLLKA DHHATNGVVH LIDKVISTIT NNIQQIIEIE DTFETLRAAV AASGLNTMLE GNGQYTLLAP TNEAFEKIPS ETLNRILGDP EALRDLLNNH ILKSAMCAEA IVAGLSVETL EGTTLEVGCS GDMLTINGKA IISNKDILAT NGVIHYIDEL LIPDSAKTLF ELAAESDVST AIDLFRQAGL GNHLSGSERL TLLAPLNSVF KDGTPPIDAH TRNLLRNHII KDQLASKYLY HGQTLETLGG KKLRVFVYRN SLCIENSCIA AHDKRGRYGT LFTMDRVLTP PMGTVMDVLK GDNRFSMLVA AIQSAGLTET LNREGVYTVF APTNEAFRAL PPRERSRLLG DAKELANILK YHIGDEILVS GGIGALVRLK SLQGDKLEVS LKNNVVSVNK EPVAEPDIMA TNGVVHVITN VLQPPANRPQ ERGDELADSA LEIFKQASAF SRASQRSVRL APVYQKLLER MKH |
| 2 (βig-h3 nucleic acid sequence) | ctccttgcac gggccggccc agcttcccg ccctggcgt ccgctccctc ccgctcgcag cttacttaac ctgccccggg cggcggaggc gctctcactt ccctggagcc gcccgcttgc ccgtcggtcg ctagctcgct cggtgcgcgt cgtcccgctc catgcgctc ttcgtgcggc tgctggctct cgccctggct ctggccctgg gccccgccgc gacccctggcg ggtcccgcca agtcgccta ccagctggtg ctgcagcaca gcaggctccg gggccgccag cacggcccca acgtgtgtgc tgtgcagaag gttattggca ctaataggaa gtacttcacc aactgcaagc agtggtacca aaggaaaatc tgtggcaaat caacagtcat cagctacgag tgctgtcctg gatatgaaaa ggtcctggg gagaagggct gtccagcagc cctaccactc tcaaaccttt acgagaccct gggagtcgtt ggatccacca ccactcagct gtacacggac cgcacggaga agctgaggcc tgagatggag gggccggca gcttccaccat cttcgccct agcaacgagg cctgggcctc cttgccagct gaagtgctgg actccctggt cagcaatgtc aacattgagc tgctcaatgc cctccgctac catatggtgg gcaggcgagt cctgactgat gagctgaaac acggcatgac cctcaccct atgtaccaga attccaacat ccagatccac cactatccta atgggattgt aactgtgaac tgtgcccggc tgctgaaagc cgaccaccat gcaaccaacg gggtggtgca cctcatcgat aaggtcatct ccaccatcac caacaacatc cagcagatca ttgagatcga ggacaccttt gagacccttc gggctgctgt ggctgcatca gggctcaaca cgatgcttga aggtaacggc cagtacacgc tttggcccc gaccaatgag gccttcgaga agatccctag tgagactttg aaccgtatcc tgggcgaccc agaagccctg agagacctgc tgaacaacca catcttgaag tcagctatgt gtgctgaagc catcgttgcg gggctgtctg tagagaccct ggagggcacg acactggagg tgggctgcag cggggacatg ctcactatca acgggaaggc gatcatctcc aataaagaca tcctagccac caacgggtg atccactaca ttgatgagct actcatccca gactcagcca agacactatt tgaattggct gcagagtctg atgtgtccac agccattgac ctrttcagac aagccggcct cggcaatcat ctctctggaa gtgagcggtt gaccctcctg gctccctga attctgtat caaagatgga accctccaa ttgatgccca tacaaggaat ttgcttcgga accacataat taaagaccag ctggcctcta agtatctgta ccatggacag accctgaaa ctctgggcgg caaaaaactg agagttttg ttatcgtaa tagcctctgc attgagaaca gctgcatcgc ggcccacgac aagagggga ggtacgggac cctgttcacg atggaccggg tgctgacccc cccaatgggg actgtcatgg atgtcctgaa gggagacaat cgctttagca tgctggtagc tgccatccag tctgcaggac tgacggagac cctcaaccgg gaaggagtct acacagtctt tgctcccaca aatgaagcct tccgagccct gccaccaaga gactcttggg agatgccaag gaacttgcca acatcctgaa ataccacatt ggtgatgaaa tcctggttag cggaggcatc ggggcctgg tgcggctaaa gtctctccaa ggtgacaagc tggaagtcag cttgaaaaac aatgtggtga gtgtcaacaa ggagcctgtt gccgagcctg acatcatggc cacaaatggc gtggtccatg tcatccacaa tgttctgcag cctccagcca acagacctca ggaaagaggg gatgaacttg cagactctgc gcttgagatc ttcaaacaag catcagcgtt ttccagggct tccagaggt ctgtgcgact agccctgtc tatcaaaagt tattagagag gatgaagcat |

TABLE 1-continued

Useful nucleotide and amino acid
sequences for practicing the invention

| SEQ ID NO | Nucleotide or amino acid sequence |
|---|---|
| | tagcttgaag cactacagga ggaatgcacc acggcagctc tccgccaatt tctctcagat ttccacagag<br>actgtttgaa tgttttcaaa accaagtatc acactttaat gtacatgggc cgcaccataa tgagatgtga<br>gccttgtgca tgtggggggag gagggagaga gatgtacttt ttaaatcatg ttccccctaa acatggctgt<br>taacccactg catgcagaaa cttggatgtc actgcctgac attcacttcc agagaggacc tatcccaaat<br>gtggaattga ctgcctatgc caagtccctg gaaaaggagc ttcagtattg tggggctcat aaaacatgaa<br>tcaagcaatc cagcctcatg ggaagtcctg gcacagtttt tgtaaagccc ttgcacagct ggagaaatgg<br>catcattata agctatgagt tgaaatgttc tgtcaaatgt gtctcacatc tacacgtggc ttggaggctt<br>ttatggggcc ctgtccaggt agaaaagaaa tggtatgtag agcttagatt tccctattgt gacagagcca<br>tggtgtgttt gtaataataa aaccaaagaa acata |
| 3<br>(TBPi Forward primer) | TGGTGTGCACAGGAGCCAAG |
| 3<br>(TBPi Reverse primer) | TTCACATCACAGCTCCCCAC |

REFERENCES

Throughout this application, various references describe the state of the art to which this invention pertains. The disclosures of these references are hereby incorporated by reference into the present disclosure.

---

The invention claimed is:

1. A method of treating a patient afflicted with pancreatic ductal adenocarcinoma having a stroma comprising cancer associated fibroblasts producing transforming growth factor β-induced protein (βig-h3), comprising
selecting an anti-βig-h3 neutralizing antibody capable of binding to stroma-produced βig-h3 protein and inhibiting interaction between stroma-produced βig-h3 protein and αVβ3 integrin,
administering to the patient a therapeutically effective amount of the anti-βig-h3 neutralizing antibody binding to stroma-produced βig-h3 protein and inhibiting interaction between stroma-produced βig-h3 protein and αVβ3 integrin,
obtaining specific binding of said anti-βig-h3 neutralizing antibody to stroma-produced βig-h3,
inhibiting interaction between stroma-produced βig-h3 protein and αVβ3 integrin, and
inhibiting the inhibition of cluster of differentiation 8 (CD8)+T cell activation.

2. A method to activate the anti-tumoral cluster of differentiation 8 (CD8)+T cell response of a patient affected with a cancer having a stroma comprising cancer associated fibroblasts expressing or secreting a transforming growth factor β-induced protein (βig-h3), comprising selecting an anti-βig-h3 neutralizing antibody capable of inhibiting interaction between stroma-produced βig-h3 protein and αVβ3 integrin, and administering to the patient a therapeutically effective amount of the anti-βig-h3 neutralizing antibody inhibiting interaction between βig-h3 protein and αVβ3 integrin.

3. The method according to claim 2, wherein the cancer is a solid tumor selected from the group consisting of pancreatic cancer, esophageal cancer, squamous cell carcinoma, gastric carcinoma, hepatic carcinoma, colon cancer, and melanoma.

4. The method according to claim 3, wherein the solid tumor is pancreatic cancer.

5. The method according to claim 3 wherein the pancreatic cancer is pancreatic ductal adenocarcinoma.

6. A method of reducing of tumor growth in vivo or inducing neutralization of tumor growth in vivo in a patient afflicted with pancreatic ductal adenocarcinoma having a stroma comprising cancer associated fibroblasts producing βig-h3 protein, comprising selecting an anti-βig-h3 neutralizing antibody capable of binding to stroma-produced βig-h3 protein and inhibiting interaction between stroma-produced βig-h3 protein and αVβ3 integrin, administering to the patient a therapeutically effective amount of the anti-βig-h3 neutralizing antibody inhibiting interaction between βig-h3 protein and αVβ3 integrin, obtaining specific binding of said anti-βig-h3 neutralizing antibody to stroma-expressed βig-h3, inhibiting interaction between stroma-produced βig-h3 protein and αVβ3 integrin, and inhibiting the inhibition of cluster of differentiation 8 (CD8)+T cell activation.

7. A method to activate the anti-tumoral cluster of differentiation 8 (CD8)+T cell response of a patient affected with a cancer having a stroma comprising cancer associated fibroblasts expressing or secreting a transforming growth factor β-induced protein (βig-h3) and obtaining anti-transforming growth factor β-induced protein (βig-h3) neutralizing effect on tumor growth in vivo, comprising selecting an anti-βig-h3 neutralizing antibody capable of inhibiting interaction between stroma-produced βig-h3 protein and αVβ3 integrin, administering to the patient a therapeutically effective amount of the anti-βig-h3 neutralizing antibody inhibiting interaction between βig-h3 protein and αVβ3 integrin, inhibiting interaction between stroma-produced βig-h3 protein and αVβ3 integrin, wherein tumor growth in vivo is reduced.

8. The method of claim 7, further comprising the step of inhibiting tumor cell growth.

9. The method according to claim 7, wherein the cancer is a solid tumor selected from the group consisting of pancreatic cancer, esophageal cancer, squamous cell carcinoma, gastric carcinoma, hepatic carcinoma, colon cancer, and melanoma.

10. The method according to claim 9, wherein the solid tumor is pancreatic cancer.

11. The method according to claim 9, wherein the pancreatic cancer is pancreatic ductal adenocarcinoma.

12. A method of treating a patient afflicted with pancreatic ductal adenocarcinoma having a stroma comprising cancer associated fibroblasts producing βig-h3 protein, comprising selecting an anti-βig-h3 neutralizing antibody capable of binding to stroma-produced βig-h3 protein and inhibiting interaction between stroma-produced βig-h3 protein and αVβ3 integrin, administering to the patient a therapeutically effective amount of the anti-βig-h3 neutralizing antibody specifically binding to βig-h3, and neutralizing an interaction between βig-h3 protein and αVβ3 integrin.

* * * * *

SEQUENCE LISTING

<160> NUMBER OF SEQ ID NOS: 4

<210> SEQ ID NO 1
<211> LENGTH: 683
<212> TYPE: PRT
<213> ORGANISM: Homo sapiens

<400> SEQUENCE: 1

```
Met Ala Leu Phe Val Arg Leu Leu Ala Leu Ala Leu Ala Leu
1               5                   10                  15

Gly Pro Ala Ala Thr Leu Ala Gly Pro Ala Lys Ser Pro Tyr Gln Leu
                20                  25                  30

Val Leu Gln His Ser Arg Leu Arg Gly Arg Gln His Gly Pro Asn Val
            35                  40                  45

Cys Ala Val Gln Lys Val Ile Gly Thr Asn Arg Lys Tyr Phe Thr Asn
    50                  55                  60

Cys Lys Gln Trp Tyr Gln Arg Lys Ile Cys Gly Lys Ser Thr Val Ile
65                  70                  75                  80

Ser Tyr Glu Cys Cys Pro Gly Tyr Glu Lys Val Pro Gly Glu Lys Gly
                85                  90                  95

Cys Pro Ala Ala Leu Pro Leu Ser Asn Leu Tyr Glu Thr Leu Gly Val
                100                 105                 110

Val Gly Ser Thr Thr Thr Gln Leu Tyr Thr Asp Arg Thr Glu Lys Leu
            115                 120                 125

Arg Pro Glu Met Glu Gly Pro Gly Ser Phe Thr Ile Phe Ala Pro Ser
        130                 135                 140

Asn Glu Ala Trp Ala Ser Leu Pro Ala Glu Val Leu Asp Ser Leu Val
145                 150                 155                 160

Ser Asn Val Asn Ile Glu Leu Leu Asn Ala Leu Arg Tyr His Met Val
```

```
                165                 170                 175
Gly Arg Arg Val Leu Thr Asp Glu Leu Lys His Gly Met Thr Leu Thr
            180                 185                 190

Ser Met Tyr Gln Asn Ser Asn Ile Gln Ile His His Tyr Pro Asn Gly
            195                 200                 205

Ile Val Thr Val Asn Cys Ala Arg Leu Leu Lys Ala Asp His His Ala
            210                 215                 220

Thr Asn Gly Val Val His Leu Ile Asp Lys Val Ile Ser Thr Ile Thr
225                 230                 235                 240

Asn Asn Ile Gln Gln Ile Ile Glu Ile Glu Asp Thr Phe Glu Thr Leu
                245                 250                 255

Arg Ala Ala Val Ala Ala Ser Gly Leu Asn Thr Met Leu Glu Gly Asn
            260                 265                 270

Gly Gln Tyr Thr Leu Leu Ala Pro Thr Asn Glu Ala Phe Glu Lys Ile
            275                 280                 285

Pro Ser Glu Thr Leu Asn Arg Ile Leu Gly Asp Pro Glu Ala Leu Arg
            290                 295                 300

Asp Leu Leu Asn Asn His Ile Leu Lys Ser Ala Met Cys Ala Glu Ala
305                 310                 315                 320

Ile Val Ala Gly Leu Ser Val Glu Thr Leu Glu Gly Thr Thr Leu Glu
                325                 330                 335

Val Gly Cys Ser Gly Asp Met Leu Thr Ile Asn Gly Lys Ala Ile Ile
            340                 345                 350

Ser Asn Lys Asp Ile Leu Ala Thr Asn Gly Val Ile His Tyr Ile Asp
            355                 360                 365

Glu Leu Leu Ile Pro Asp Ser Ala Lys Thr Leu Phe Glu Leu Ala Ala
370                 375                 380

Glu Ser Asp Val Ser Thr Ala Ile Asp Leu Phe Arg Gln Ala Gly Leu
385                 390                 395                 400

Gly Asn His Leu Ser Gly Ser Glu Arg Leu Thr Leu Leu Ala Pro Leu
            405                 410                 415

Asn Ser Val Phe Lys Asp Gly Thr Pro Pro Ile Asp Ala His Thr Arg
            420                 425                 430

Asn Leu Leu Arg Asn His Ile Ile Lys Asp Gln Leu Ala Ser Lys Tyr
            435                 440                 445

Leu Tyr His Gly Gln Thr Leu Glu Thr Leu Gly Gly Lys Lys Leu Arg
            450                 455                 460

Val Phe Val Tyr Arg Asn Ser Leu Cys Ile Glu Asn Ser Cys Ile Ala
465                 470                 475                 480

Ala His Asp Lys Arg Gly Arg Tyr Gly Thr Leu Phe Thr Met Asp Arg
            485                 490                 495

Val Leu Thr Pro Pro Met Gly Thr Val Met Asp Val Leu Lys Gly Asp
            500                 505                 510

Asn Arg Phe Ser Met Leu Val Ala Ala Ile Gln Ser Ala Gly Leu Thr
            515                 520                 525

Glu Thr Leu Asn Arg Glu Gly Val Tyr Thr Val Phe Ala Pro Thr Asn
530                 535                 540

Glu Ala Phe Arg Ala Leu Pro Pro Arg Glu Arg Ser Arg Leu Leu Gly
545                 550                 555                 560

Asp Ala Lys Glu Leu Ala Asn Ile Leu Lys Tyr His Ile Gly Asp Glu
            565                 570                 575

Ile Leu Val Ser Gly Gly Ile Gly Ala Leu Val Arg Leu Lys Ser Leu
            580                 585                 590
```

```
Gln Gly Asp Lys Leu Glu Val Ser Leu Lys Asn Asn Val Ser Val
        595                 600                 605

Asn Lys Glu Pro Val Ala Glu Pro Asp Ile Met Ala Thr Asn Gly Val
    610                 615                 620

Val His Val Ile Thr Asn Val Leu Gln Pro Pro Ala Asn Arg Pro Gln
625                 630                 635                 640

Glu Arg Gly Asp Glu Leu Ala Asp Ser Ala Leu Glu Ile Phe Lys Gln
            645                 650                 655

Ala Ser Ala Phe Ser Arg Ala Ser Gln Arg Ser Val Arg Leu Ala Pro
        660                 665                 670

Val Tyr Gln Lys Leu Leu Glu Arg Met Lys His
        675                 680

<210> SEQ ID NO 2
<211> LENGTH: 2805
<212> TYPE: DNA
<213> ORGANISM: Homo sapiens

<400> SEQUENCE: 2
ctccttgcac gggccggccc agcttccccg cccctggcgt ccgctccctc ccgctcgcag      60
cttacttaac ctggcccggg cggcggaggc gctctcactt ccctggagcc gcccgcttgc     120
ccgtcggtcg ctagctcgct cggtgcgcgt cgtcccgctc catggcgctc ttcgtgcggc     180
tgctggctct cgccctggct ctggccctgg gccccgccgc gaccctggcg gtcccgcca      240 agtcgcccta ccagctggtg ctgcagcaca gcaggctccg gggccgccag cacggcccca     300
acgtgtgtgc tgtgcagaag gttattggca ctaataggaa gtacttcacc aactgcaagc     360
agtggtacca aggaaaatc tgtggcaaat caacagtcat cagctacgag tgctgtcctg     420
gatatgaaaa ggtccctggg gagaagggct gtccagcagc cctaccactc tcaaaccttt     480
acgagaccct gggagtcgtt ggatccacca ccactcagct gtacacggac cgcacggaga     540
agctgaggcc tgagatggag gggcccggca gcttcaccat cttcgcccct agcaacgagg     600
cctgggcctc cttgccagct gaagtgctgg actccctggt cagcaatgtc aacattgagc     660
tgctcaatgc cctccgctac catatggtgg gcaggcgagt cctgactgat gagctgaaac     720
acggcatgac cctcaccctct atgtaccaga attccaacat ccagatccac cactatccta     780
atgggattgt aactgtgaac tgtgccccggc tgctgaaagc cgaccaccat gcaaccaacg     840
gggtggtgca cctcatcgat aaggtcatct ccaccatcac caacaacatc cagcagatca     900
ttgagatcga ggacaccttt gagacccttc gggctgctgt ggctgcatca gggctcaaca     960
cgatgcttga aggtaacggc cagtacacgc ttttggcccc gaccaatgag gccttcgaga    1020
agatccctag tgagactttg aaccgtatcc tgggcgaccc agaagccctg agagacctgc    1080
tgaacaacca catcttgaag tcagctatgt gtgctgaagc catcgttgcg ggctgtctg     1140 tagagaccct ggagggcacg acactggagg tgggctgcag cggggacatg ctcactatca    1200
acgggaaggc gatcatctcc aataaagaca tcctagccac caacggggtg atccactaca    1260
ttgatgagct actcatccca gactcagcca agacactatt tgaattggct gcagagtctg    1320
atgtgtccac agccattgac cttttcagac aagccggcct cggcaatcat ctctctggaa    1380
gtgagcggtt gaccctcctg gctcccctga attctgtatt caaagatgga acccctccaa    1440
ttgatgccca tacaaggaat ttgcttcgga accacataat aaagaccag ctggcctcta    1500 agtatctgta ccatggacag accctggaaa ctctgggcgg caaaaaactg agagttttg     1560
```

```
tttatcgtaa tagcctctgc attgagaaca gctgcatcgc ggcccacgac aagaggggga    1620
ggtacgggac cctgttcacg atggaccggg tgctgacccc cccaatgggg actgtcatgg    1680
atgtcctgaa gggagacaat cgctttagca tgctggtagc tgccatccag tctgcaggac    1740
tgacggagac cctcaaccgg gaaggagtct acacagtctt tgctcccaca aatgaagcct    1800
tccgagccct gccaccaaga gaacggagca gactcttggg agatgccaag gaacttgcca    1860
acatcctgaa ataccacatt ggtgatgaaa tcctggttag cggaggcatc ggggccctgg    1920
tgcggctaaa gtctctccaa ggtgacaagc tggaagtcag cttgaaaaac aatgtggtga    1980
gtgtcaacaa ggagcctgtt gccgagcctg acatcatggc cacaaatggc gtggtccatg    2040
tcatcaccaa tgttctgcag cctccagcca acagacctca ggaagagggg gatgaacttg    2100
cagactctgc gcttgagatc ttcaaacaag catcagcgtt ttccagggct tcccagaggt    2160
ctgtgcgact agcccctgtc tatcaaaagt tattagagag gatgaagcat tagcttgaag    2220
cactacagga ggaatgcacc acggcagctc tccgccaatt tctctcagat ttccacagag    2280
actgtttgaa tgttttcaaa accaagtatc acactttaat gtacatgggc cgcaccataa    2340
tgagatgtga gccttgtgca tgtggggag gagggagaga gatgtacttt ttaaatcatg    2400
ttccccctaa acatggctgt taacccactg catgcagaaa cttggatgtc actgcctgac    2460
attcacttcc agagaggacc tatcccaaat gtggaattga ctgcctatgc caagtccctg    2520
gaaaaggagc ttcagtattg tggggctcat aaaacatgaa tcaagcaatc cagcctcatg    2580
ggaagtcctg gcacagtttt tgtaaagccc ttgcacagct ggagaaatgg catcattata    2640
agctatgagt tgaaatgttc tgtcaaatgt gtctcacatc tacacgtggc ttggaggctt    2700
ttatggggcc ctgtccaggt agaaaagaaa tggtatgtag agcttagatt tccctattgt    2760
gacagagcca tggtgtgttt gtaataataa aaccaaagaa acata                    2805

<210> SEQ ID NO 3
<211> LENGTH: 20
<212> TYPE: DNA
<213> ORGANISM: Artificial
<220> FEATURE:
<223> OTHER INFORMATION: Synthetic TBPi Forward primer

<400> SEQUENCE: 3
tggtgtgcac aggagccaag                                                20

<210> SEQ ID NO 4
<211> LENGTH: 20
<212> TYPE: DNA
<213> ORGANISM: Artificial
<220> FEATURE:
<223> OTHER INFORMATION: Synthetic TBPi Reverse primer

<400> SEQUENCE: 4
ttcacatcac agctccccac                                                20
```